US012605315B2

(12) United States Patent
Fukui et al.

(10) Patent No.: US 12,605,315 B2
(45) **Date of Patent: *Apr. 21, 2026**

(54) EXTERNAL SKIN PREPARATION

(71) Applicant: KAO CORPORATION, Tokyo (JP)

(72) Inventors: Takashi Fukui, Kawasaki (JP); Noriko Tejima, Sumida-ku (JP)

(73) Assignee: KAO CORPORATION, Tokyo (JP)

( * ) Notice: Subject to any disclaimer, the term of this patent is extended or adjusted under 35 U.S.C. 154(b) by 891 days.

This patent is subject to a terminal disclaimer.

(21) Appl. No.: 17/417,573

(22) PCT Filed: Dec. 27, 2019

(86) PCT No.: PCT/JP2019/051463

§ 371 (c)(1),
(2) Date: Jun. 23, 2021

(87) PCT Pub. No.: WO2020/138429

PCT Pub. Date: Jul. 2, 2020

(65) Prior Publication Data

US 2022/0054376 A1 Feb. 24, 2022

(30) Foreign Application Priority Data

Dec. 27, 2018 (JP) ................................ 2018-244996
Dec. 27, 2018 (JP) ................................ 2018-244997

(51) Int. Cl.

*A61K 8/29* (2006.01)
*A61K 8/27* (2006.01)
*A61K 8/92* (2006.01)
*A61Q 17/04* (2006.01)

(52) U.S. Cl.

CPC ................. *A61K 8/29* (2013.01); *A61K 8/27* (2013.01); *A61K 8/92* (2013.01); *A61Q 17/04* (2013.01); *A61K 2800/413* (2013.01); *A61K 2800/522* (2013.01)

(58) Field of Classification Search

CPC ... A61K 8/29; A61K 8/27; A61K 8/92; A61K 2800/413; A61K 2800/522; A61Q 17/04
See application file for complete search history.

(56) References Cited

U.S. PATENT DOCUMENTS

| | | | | |
|---|---|---|---|---|
| 2005/0266057 | A1* | 12/2005 | Hagura .................. | A61Q 19/00 424/443 |
| 2012/0027830 | A1* | 2/2012 | Nakamura ............... | A61K 8/19 977/773 |
| 2018/0280283 | A1* | 10/2018 | Kojima .................... | A61K 8/37 |
| 2020/0172407 | A1 | 6/2020 | Yoshida et al. | |

FOREIGN PATENT DOCUMENTS

| | | | |
|---|---|---|---|
| EP | 2233127 | | 5/2020 |
| JP | 62-4212 | A | 1/1987 |
| JP | 62-149613 | A | 7/1987 |
| JP | 5-25028 | A | 2/1993 |
| JP | 7-173044 | A | 7/1995 |
| JP | 10-95617 | A | 4/1998 |
| JP | 10-182397 | A | 7/1998 |
| JP | 2003-192338 | A | 7/2003 |
| JP | 2004-203768 | A | 7/2004 |
| JP | 2006-151917 | A | 6/2006 |
| JP | 2006-282510 | A | 10/2006 |
| JP | 2017-95361 | A | 6/2017 |
| JP | 2017-155006 | A | 9/2017 |
| JP | 2017-171655 | A | 9/2017 |
| WO | WO 2009/017104 | A1 | 2/2009 |
| WO | WO 2011/055761 | A1 | 5/2011 |
| WO | WO 2011/055771 | A1 | 5/2011 |
| WO | WO 2015/033990 | A1 | 3/2015 |
| WO | WO 2018/230472 | A1 | 12/2018 |

OTHER PUBLICATIONS

Jiang Shiliang et al., "Frontiers in Physics and High Technology," Guangxi Nationalities Publishing House, Sep. 2006, 5 pages (with English machine translation).
Xiaoxin et al., "Sunscreen", NTU, Jul. 26, 2011, 6 pages (with unedited computer-generated English Translation).
Extended European Search Report issued Oct. 7, 2022 in European Patent Application No. 19901829.2, 7 pages.
International Search Report issued on Mar. 17, 2020 in PCT/JP2019/051463 filed on Dec. 27, 2019, 3 pages.

* cited by examiner

*Primary Examiner* — Robert A Wax
*Assistant Examiner* — Olga V. Tcherkasskaya
(74) *Attorney, Agent, or Firm* — Oblon, McClelland, Maier & Neustadt, L.L.P.

(57) ABSTRACT

The present invention relates to [1] an external skin preparation containing a tabular metal oxide (A) having a thickness of 30 to 360 nm and an aspect ratio of 50 to 300, and a UV absorbent (B) in a ratio [(A)/(B)] by mass of 0.1 to 5; [2] an external skin reparation containing the tabular metal oxide (A), a UV scattering agent (C) and a nonvolatile oil (D) in a ratio [(A)/(C)] by mass of 0.1 to 18; and [3] a method for protecting skin from IR rays and UV rays by applying the external skin preparation to skin.

11 Claims, No Drawings

EXTERNAL SKIN PREPARATION

FIELD OF THE INVENTION

The present invention relates to an external skin preparation, and a method for protecting skin from IR rays and UV rays.

BACKGROUND OF THE INVENTION

From the viewpoint of protecting skin from sunlight, UV protective cosmetics such as sunblock cosmetics are known. On the other hand, with the recent increase in health consciousness, an external skin preparation having a protective function against IR rays has become desired.

Regarding such an external skin preparation having an IR protective function, for example, WO2009/017104 (Patent Literature 1) discloses a near-IR damage protective agent for body tissues, which contains an IR transmission masking agent of a titanium oxide powder and a zinc oxide powder, as a technique relating to an inhibitor that inhibits IR rays from reaching a tissue deeper than a skin tissue to thereby prevent the tissues from damage by IR rays.

Also, JP2017-95361 A (Patent Literature 2) discloses a near IR protective cosmetic composition containing a titanium oxide powder and a zinc oxide powder, which satisfies both an excellent near IR protective effect and a high transparency.

SUMMARY OF THE INVENTION

The present invention relates to [1] an external skin preparation (I) containing a tabular metal oxide (A) having a thickness of 30 nm or more and 360 nm or less and an aspect ratio of 50 or more and 300 or less, and a UV absorbent (B) in a ratio [(A)/(B)] by mass of 0.1 or more and 5 or less, [2] an external skin preparation (II) containing a tabular metal oxide (A) having a thickness of 30 nm or more and 360 nm or less and an aspect ratio of 50 or more and 300 or less, a UV scattering agent (C) and a nonvolatile oil (D) in a ratio [(A)/(C)] by mass of 0.1 or more and 18 or less, and [3] a method for protecting skin from IR rays and UV rays by applying the external skin preparation to skin.

DETAILED DESCRIPTION OF THE INVENTION

For skin protection, an external skin preparation capable of further improving an IR protective function and excellent in a UV protective effect is desired. Among external skin preparations, a skin cosmetic material is further desired to be such that (I) when applied to skin, it hardly whitens and can give a natural appearance, and after applied, it secures a good adhesion of makeup and is excellent in a sense of use with little stickiness, or (II) after applied, it secures a good adhesion of makeup and is excellent in a sense of use.

The present invention relates to an external skin preparation (I) excellent in an IR protective effect and a UV protective effect, which, when applied to skin, hardly whitens and can give a natural appearance, and which, after applied, secures a good adhesion of makeup and is excellent in a sense of use with little stickiness, to an external skin preparation (II) excellent in an IR protective effect and a UV protective effect, which, when applied to skin, hardly whitens and can give a natural appearance, and which, after applied, secures a good adhesion of makeup, and to a method for protecting skin from IR rays and UV rays.

The present inventors have found that an external skin preparation (I) containing a metal oxide having a predetermined shape and a UV absorbent in a predetermined ratio, and an external skin preparation (II) containing a metal oxide having a predetermined shape and a UV scattering agent in a predetermined ratio, and further containing a nonvolatile oil can solve the above-mentioned problems.

Specifically, the present invention relates to the following [1] to [3].

[1] An external skin preparation (I) containing a tabular metal oxide (A) having a thickness of 30 nm or more and 360 nm or less and an aspect ratio of 50 or more and 300 or less, and a UV absorbent (B) in a ratio [(A)/(B)] by mass of 0.1 or more and 5 or less.

[2] An external skin preparation (II) containing a tabular metal oxide (A) having a thickness of 30 nm or more and 360 nm or less and an aspect ratio of 50 or more and 300 or less, a UV scattering agent (C) and a nonvolatile oil (D) in a ratio [(A)/(C)] by mass of 0.1 or more and 18 or less.

[3] A method for protecting skin from IR rays and UV rays by applying the external skin preparation of [1] or [2] to skin.

The external skin preparation (I) of the present invention is excellent in an IR and UV protective effect, and when applied to skin, hardly whitens and can give a natural appearance, and after applied, secures a good adhesion of makeup and is excellent in a sense of use with little stickiness, and is therefore useful, for example, as a skin cosmetic material.

Also, the external skin preparation (II) of the present invention is excellent in an IR and UV protective effect, and when applied to skin, hardly whitens and can give a natural appearance, and after applied, secures a good adhesion of makeup and is excellent in a sense of use, and is therefore useful, for example, as a skin cosmetic material.

[External Skin Preparation]

The external skin preparation (I) of the present invention contains a tabular metal oxide (A) having a thickness of 30 nm or more and 360 nm or less and an aspect ratio of 50 or more and 300 or less, and a UV absorbent (B) in a ratio [(A)/(B)] by mass of 0.1 or more and 5 or less.

The external skin preparation (II) of the present invention contains a tabular metal oxide (A) having a thickness of 30 nm or more and 360 nm or less and an aspect ratio of 50 or more and 300 or less, a UV scattering agent (C) and a nonvolatile oil (D) in a ratio [(A)/(C)] by mass of 0.1 or more and 18 or less.

In the present invention, the thickness of the tabular metal oxide means a length of the shortest axis in a tabular metal oxide particle.

In the present invention, UV rays mean electromagnetic waves having a wavelength of 290 to 400 nm.

Also in the present invention, IR rays mean electromagnetic waves having a wavelength of 780 nm to 1 mm. Among these, the external skin preparation of the present invention is especially excellent in an effect of protecting from near IR rays having a wavelength of 780 nm to 2500 nm. Accordingly, the external skin preparation of the present invention can prevent increase in the skin temperature by sunlight irradiation, and can realize an actual sensation of high-level heat insulation.

In this description, an IR protection factor at a wavelength of 1500 nm is used as an index for the IR protective effect; and an SPF (sun protection factor) (protective effect from UV-B waves (UVB)) is used as an index for the UV protective effect.

The dosage form of the external skin preparation of the present invention is not specifically limited, but is, from the viewpoint of applicability to skin, preferably liquid, gel or cream. The external skin preparation may also be in a form of an emulsified composition, and the emulsified composition may be any of an oil-in-water type emulsified composition or a water-in-oil type emulsified composition.

The external skin preparation of the present invention is preferably a skin cosmetic material such as a sunblock cosmetic material (lotion, cream, emulsion, serum, etc.), a suntan lotion, a makeup foundation material, etc.

<Tabular Metal Oxide (A)>

The external skin preparation of the present invention contains a tabular metal oxide (A) having a thickness of 30 nm or more and 360 nm or less and an aspect ratio of 50 or more and 300 or less.

Containing such a tabular metal oxide having a predetermined thickness as the component (A), the external skin preparation of the present invention is excellent in an IR protective effect and can realize an actual sensation of high-level heat insulation, and in addition, when applied to skin, it hardly whitens and can give a natural appearance. Further, when applied to skin, it prevents stickiness.

It is known that an external skin preparation containing inorganic particles of titanium oxide or the like can have a higher IR protective effect when the inorganic particles therein have a large particle size. However, mere use of inorganic particles having a large particle size is limited in improving the IR protective effect. In addition, for example, in the case where spherical inorganic particles having a particle size larger than the wavelength of visible light are blended in an external skin preparation and when the external skin preparation is applied to skin, it may often whiten owing to visible light scattering on the surfaces of the particles therein, therefore providing a problem of giving a sense of inferiority in natural appearance. Consequently, when the particle size of the inorganic particles to be used is merely controlled, it is still difficult to satisfy both the IR protective effect and the natural sense of appearance in applying the preparation to skin.

The present inventors have found that, when a tabular metal oxide having a predetermined thickness is used as the component (A) in an external skin preparation, it is possible to reduce the reflectance of light in a visible region while selectively increasing the reflectance of light in an IR region by the interference effect of light, and accordingly, it becomes possible to satisfy both the IR protective effect and the natural sense of appearance in applying the preparation to skin.

When the thickness of the component (A) falls within the above-mentioned predetermined range (30 nm or more and 360 nm or less), and when an external preparation containing the component (A) is applied to skin, the reflectance of light to be observed on the side of the skin surface can be such that the reflectance of light having a wavelength in an IR region is high while that of light having a wavelength in a visible region is low owing to the interference effect of light. Consequently, the external skin preparation of the present invention can satisfy both a high IR protective effect and a sense of natural appearance when applied to skin.

Using the above-mentioned predetermined component (A) also betters a good adhesion of makeup after the preparation is applied to skin. Further, combined use of the component (A) and a UV absorbent (B) provides an effect of synergistically enhancing the UV protective effect.

Also further, combined use of the component (A) and UV scattering agent (C) provides an effect of synergistically enhancing the UV protective effect.

From the viewpoint of achieving an excellent IR protective effect and an excellent UV protective effect owing to the above-mentioned mechanism of action, and from the viewpoint of a sense of natural appearance when applied to skin, the thickness of the component (A) is 30 nm or more, preferably 50 nm or more, more preferably 60 nm or more, even more preferably 80 nm or more, further more preferably 105 nm or more, further more preferably 125 nm or more. Also from the viewpoint of achieving an excellent IR protective effect and an excellent UV protective effect, and from the viewpoint of a sense of natural appearance when applied to skin, and a good adhesion of makeup after applied to skin, the thickness of the component (A) is 360 nm or less, preferably 330 nm or less, more preferably 310 nm or less, even more preferably 280 nm or less, further more preferably 270 nm or less, further more preferably 230 nm or less, further more preferably 150 nm or less. A specific range of the thickness of the component (A) is, from the viewpoint of achieving an excellent IR protective effect and an excellent UV protective effect, and from the viewpoint of a sense of natural appearance when applied to skin, and a good adhesion of makeup after applied to skin, 30 nm or more and 360 nm or less, preferably 50 nm or more and 330 nm or less, more preferably 60 nm or more and 310 nm or less, even more preferably 60 nm or more and 280 nm or less, further more preferably 80 nm or more and 280 nm or less, further more preferably 105 nm or more and 270 nm or less, further more preferably 125 nm or more and 270 nm or less, further more preferably 125 nm or more and 230 nm or less, further more preferably 125 nm or more and 150 nm or less.

The thickness of the component (A) can be determined on an image observed with a scanning electronic microscope (SEM). Specifically, the component (A) is observed with SEM under the condition of an observation magnification of 10,000 times, the thickness of 50 particles in the observed image is measured individually, and the found data of the thickness are averaged to give an average of the thickness per number of particles. Specifically, the thickness of the component (A) can be measured according to the method described in the section of Examples.

In the case of the external skin preparation (I), from the viewpoint of achieving an excellent IR protective effect and an excellent UV protective effect, and from the viewpoint of a sense of natural appearance when applied to skin, and a good adhesion of makeup after applied to skin, the aspect ratio of the component (A) is 50 or more, preferably 55 or more, more preferably 65 or more, even more preferably 70 or more, further more preferably 100 or more. Also from the viewpoint of achieving an excellent IR protective effect and an excellent UV protective effect, and from the viewpoint of a sense of natural appearance when applied to skin, the aspect ratio is 300 or less, preferably 230 or less, more preferably 200 or less, even more preferably 140 or less, further more preferably 125 or less, further more preferably 120 or less. A specific range of the aspect ratio of the component (A) is, from the viewpoint of achieving an excellent IR protective effect and an excellent UV protective effect, and from the viewpoint of a sense of natural appearance when applied to skin, and a good adhesion of makeup after applied to skin, 50 or more and 300 or less, preferably 50 or more and 230 or less, more preferably 55 or more and 230 or less, even more preferably 55 or more and 200 or less, further more preferably 55 or more and 140 or less, further more preferably 55 or more and 125 or less, further more preferably 65 or more and 125 or less, further more preferably 70 or more and 120 or less, further more preferably 100 or more and 125 or less.

In the case of the external skin preparation (II), from the viewpoint of achieving an excellent IR protective effect and an excellent UV protective effect, and from the viewpoint of a sense of natural appearance when applied to skin, the aspect ratio of the component (A) is 50 or more, preferably 55 or more, and is, from the viewpoint of achieving an excellent IR protective effect and an excellent UV protective effect, and from the viewpoint of a sense of natural appearance when applied to skin, and a good adhesion of makeup after applied to skin, 300 or less, preferably 230 or less, more preferably 200 or less, even more preferably 140 or less, further more preferably 125 or less, further more preferably 120 or less. A specific range of the aspect ratio of the component (A) is, from the viewpoint of achieving an excellent IR protective effect and an excellent UV protective effect, and from the viewpoint of a sense of natural appearance when applied to skin, and a good adhesion of makeup after applied to skin, 50 or more and 300 or less, preferably 50 or more and 230 or less, more preferably 55 or more and 230 or less, even more preferably 55 or more and 200 or less, further more preferably 55 or more and 140 or less, further more preferably 55 or more and 125 or less, further more preferably 55 or more and 120 or less.

The aspect ratio of the component (A) is determined as follows. Under the same condition as above, the particles are observed with SEM, the length of the shortest axis (thickness) and the length of the longest axis (long diameter) of 50 particles in the observed image are measured individually to calculate an aspect ratio (long diameter/thickness) of each particles, and the resultant data are averaged to give an average aspect ratio of the particles. Specifically, the aspect ratio of the tabular metal oxide can be measured according to the method described in the section of Examples.

The metal oxide of a high refractive index material to constitute the component (A) can realize a high light interference effect. From this viewpoint, a preferred metal oxide to constitute the component (A) is one or more selected from the group consisting of titanium oxide, zinc oxide, zirconium oxide, iron oxide, aluminum oxide, cerium oxide, etc. Among these, one or more selected from the group consisting of titanium oxide and zinc oxide are preferred, and titanium oxide is more preferred. Specifically, the component (A) is preferably one or more selected from tabular titanium oxide and tabular zinc oxide, more preferably tabular titanium oxide.

The crystal structure of titanium oxide may be any of a rutile type or an anatase type, or amorphous, but from the viewpoint of achieving an excellent IR protective effect and an actual sensation of high-level heat insulation, a rutile type is preferred.

The tabular metal oxide of the component (A) may be one not treated on the surface thereof, but for the purpose of enhancing the dispersibility thereof in the external skin preparation, it may be optionally surface-treated for hydrophobization or the like according to a known method. The tabular metal oxide of the component (A) is differentiated from those prepared by surface-treating any other particles than metal oxides with a metal oxide.

The surface-treating agent for use for surface treatment of the component (A) includes silicones; alkylalkoxysilanes; fluorine-containing compounds such as perfluoroalkyl phosphates, and perfluoroalcohols; amino acids such as N-acylglutamic acids; others such as lecithin; metal soaps; fatty acids such as stearic acid; alkyl phosphates, etc. Among these, from the viewpoint of enhancing the dispersibility of the component (A) in the external preparation, one or more selected from the group consisting of silicones and alkylalkoxysilanes are preferred.

Silicones as a surface-treating agent are not specifically limited, and examples thereof include various silicone oils such as methylpolysiloxane, dimethylpolysiloxane, methylphenylpolysiloxane, methylhydrogen polysiloxane, methylcyclopolysiloxane, octamethylcyclotetrasiloxane, decamethylcyclopentasiloxane, dodecamethylcyclohexasiloxane, octamethyltrisiloxane, tetradecamethylhexasiloxane, dimethylsiloxane-methyl(polyoxyethylene)siloxane-methyl (polyoxypropylene)siloxane copolymer, dimethylsiloxane-methyl(polyoxyethylene)siloxane copolymer, dimethylsiloxane-methyl(polyoxypropylene)siloxane copolymer, dimethylsiloxane-methylcetyloxysiloxane copolymer, dimethylsiloxane-methylstearoxysiloxane copolymer, and (alkyl acrylate/dimethicone) copolymer.

The alkylalkoxysilane as a surface-treating agent is preferably one having a linear or branched alkyl group having 6 to 20 carbon atoms, and is especially preferably octyltriethoxysilane or octyltrimethoxysilane.

From the viewpoint of improving the IR protective effect, one or more selected from the group consisting of methylpolysiloxane, dimethylpolysiloxane, methylhydrogen polysiloxane, (alkyl acrylate/dimethicone) copolymer and octyltriethoxysilane are preferred.

In the case where the component (A) is a surface-treated one, the coating amount with the surface-treating agent is, from the viewpoint of enhancing dispersibility in the external skin preparation, preferably 1% by mass or more and 9% by mass or less, more preferably 2% by mass or more and 8% by mass or less relative to the total amount of the tabular metal oxide of the component (A).

The content of the component (A) in the external skin preparation is, from the viewpoint of achieving an excellent IR protective effect and an excellent UV protective effect, and from the viewpoint of a sense of natural appearance when applied to skin, and a good adhesion of makeup after applied to skin, preferably 1% by mass or more, more preferably 3% by mass or more, even more preferably 6% by mass or more, further more preferably 8% by mass or more. Also from the viewpoint of a sense of natural appearance when applied to skin, and a good adhesion of makeup after applied to skin, the content of the component (A) in the external skin preparation is preferably 35% by mass or less, more preferably 25% by mass or less, even more preferably 17% by mass or less, further more preferably 12% by mass or less.

A specific range of the content of the component (A) in the external skin preparation is, from the viewpoint of achieving an excellent IR protective effect and an excellent UV protective effect, and from the viewpoint of satisfying both a sense of natural appearance when applied to skin and a good adhesion of makeup after applied to skin, preferably 1% by mass or more and 35% by mass or less more preferably 3% by mass or more and 25% by mass or less, even more preferably 6% by mass or more and 17% by mass or less, further more preferably 8% by mass or more and 12% by mass or less.

As the component (A), commercial products of a tabular metal oxide can be used. For example, commercial products of tabular titanium oxide include "Featheleve® PT-9001K", "Featheleve® PT-7001K", "Featheleve® PT-7401K", "Featheleve® PT-7801K", and "Featheleve® PT-7901K" from CQV Co., Ltd.

<UV Absorbent (B)>

The external skin preparation (I) of the present invention contains a UV absorbent as a component (B) from the viewpoint of achieving a UV protective effect.

The component (B) is preferably an organic UV absorbent, for which an oil-soluble organic UV absorbent or a water-soluble organic UV absorbent can be used. From the viewpoint of achieving a UV protective effect, a sense of natural appearance when applied to skin and a good adhesion of makeup after applied to skin, and from the viewpoint of preventing stickiness, the component (B) is preferably an oil-soluble organic UV absorbent. “Oil-soluble” means a solubility in water of 1 w/w % or less.

From the viewpoint of achieving the advantageous effects of the present invention, the component (B) is differentiated from an inorganic UV absorbent such as a UV absorbent prepared by coating the surface of an inorganic filler with a UV absorbent material.

The usable oil-soluble organic UV absorbent includes oil-soluble ones of a salicylate-based UV absorbent, a cinnamate-based UV absorbent, a benzoylmethane-based UV absorbent, and other organic UV absorbents.

Examples thereof include:

- a salicylate-based UV absorbent such as homomenthyl salicylate, and octyl salicylate;
- a cinnamate-based UV absorbent such as 2-ethylhexyl p-methoxycinnamate (e.g., “Uvinul® MC80” by BASF SE), glyceryl di-p-methoxycinnamate mono-2-ethylhexanoate, methyl 2,5-diisopropylcinnamate, methylbis(trimethylsiloxy)silylisopentyl trimethoxycinnamate, and isopropyl p-methoxycinnamate/diisopropylcinnamate mixture;
- a benzoylmethane-based UV absorbent such as 4-isopropyldibenzoylmethane, and 4-tert-butyl-4'-methoxydibenzoylmethane (e.g., “Parasol® 1789” by DSM Nutrition Japan K.K.);
- octocrylene (e.g., “Parasol® 340” by DSM Nutrition Japan K.K.), 2-ethylhexyl dimethoxy benzylidene dioxoimidazolidinepropionate (e.g., “Softshade® DH” by Ajinomoto Co., Inc.), 1-(3,4-dimethoxyphenyl)-4,4-dimethyl-1,3-pentanedione, cinoxate, methyl O-aminobenzoate, 3-(4-methylbenzylidene) camphor, octyltriazone, hexyl diethylaminohydroxybenzoyl benzoate (hexyl(2-(4-diethylamino-2-hydroxybenzoyl)benzoate, e.g., “Uvinul A Plus®” by BASF SE), bis-ethylhexyloxyphenol methoxyphenyl triazine (2,4-bis{[4-(2-ethylhexyloxy)-2-hydroxy]phenyl}-6-(4-methoxyphenyl)-1,3,5-triazine, e.g., “Tinosorb® S” by BASF SE), methylene bis-benzotriazolyl tetramethylbutylphenol (e.g., “Tinosorb® M” by BASF SE), and 2,4,6-tris[4-(2-ethylhexyloxycarbonyl)anilino]-1,3,5-triazine (hereinafter also referred to as “ethylhexyltriazone”, e.g., “Uvinul® T150” by BASF SE).

The usable water-soluble organic UV absorbent includes those having a solubility in water more than 1 w/w % of a salicylate-based UV absorbent, a cinnamate-based UV absorbent, a benzoylmethane-based UV absorbent and other organic UV absorbents, and examples thereof include triethanolamine salicylate, and diethanolamine p-methoxyhydrocinnamate.

Among the above, from the viewpoint of the UV protective effect thereof, the UV absorbent (B) is preferably one or more selected from the group consisting of 2-ethylhexyl p-methoxycinnamate, 4-tert-butyl-4'-methoxydibenzoylmethane, octocrylene, 2-ethylhexyl dimethoxybenzylidene dioxoimidazolidine propionate, hexyl diethylaminohydroxybenzoyl benzoate, bis-ethylhexyloxyphenol methoxyphenyl triazine, methylene bis-benzotriazolyl tetramethylbutylphenol, and 2,4,6-tris[4-(2-ethylhexyloxycarbonyl)anilino]-1,3,5-triazine, more preferably one or more selected from the group consisting of 2-ethylhexyl p-methoxycinnamate, hexyl diethylaminohydroxybenzoyl benzoate, bis-ethylhexyloxyphenol methoxyphenyl triazine, and 2,4,6-tris[4-(2-ethylhexyloxycarbonyl)anilino]-1,3,5-triazine, and from the viewpoint of protecting from both UVA and UVB, even more preferably, two or more of these are combined. One or more selected from the group consisting of 2-ethylhexyl p-methoxycinnamate, hexyl diethylaminohydroxybenzoyl benzoate, and bis-ethylhexyloxyphenol methoxyphenyl triazine are further more preferred, and still further more preferably, two or more of these are combined.

The ratio by mass of the component (A) to the component (B) [(A)/(B)] in the external skin preparation of the present invention is, from the viewpoint of achieving an excellent IR protective effect and an excellent UV protective effect, and from the viewpoint of a sense of natural appearance when applied to skin, and a good adhesion of makeup after applied to skin, preferably 0.1 or more, more preferably 0.3 or more, even more preferably 0.55 or more, further more preferably 0.7 or more. Also from the viewpoint of achieving an excellent UV protective effect, and from the viewpoint of a sense of natural appearance when applied to skin, and a good adhesion of makeup after applied to skin, the ratio is preferably 5 or less, more preferably 3.5 or less, even more preferably 2.3 or less, further more preferably 1.5 or less, further more preferably 1.2 or less. A specific range of the ratio by mass of the component (A) to the component (B) [(A)/(B)] in the external skin preparation (I) is, from the viewpoint of satisfying both an IR protective effect and a UV protective effect, and a sense of natural appearance when applied to skin, and a good adhesion of makeup after applied to skin, 0.1 or more and 5 or less, preferably 0.3 or more and 3.5 or less, even more preferably 0.3 or more and 2.3 or less, further more preferably 0.55 or more an 1.5 or less, further more preferably 0.55 or more and 1.2 or less, further more preferably 0.7 or more and 1.2 or less.

The content of the component (B) in the external skin preparation (I) of the present invention is not specifically limited so far as its amount is to make the ratio by mass [(A)/(B)] fall 0.1 or more and 5 or less, but is, from the viewpoint of achieving an excellent IR protective effect and an excellent UV protective effect, and from the viewpoint of a good adhesion of makeup after applied to skin, preferably 0.2% by mass or more, more preferably 1.5% by mass or more, even more preferably 5% by mass or more, further more preferably 7% by mass or more. Also from the viewpoint of achieving an excellent IR protective effect and a good adhesion of makeup after applied to skin, the content is preferably 30% by mass or less, more preferably 25% by mass or less, even more preferably 20% by mass or less, further more preferably 15% by mass or less. A specific range of the content of the component (B) in the external skin preparation (I) is, from the viewpoint of satisfying an IR protective effect, a good adhesion of makeup after applied to skin, and a UV protective effect, preferably 0.2% by mass or more and 30% by mass or less, more preferably 1.5% by mass or more and 25% by mass or less, even more preferably 5% by mass or more and 20% by mass or less, further more preferably 7% by mass or more and 15% by mass or less.

Also from the viewpoint of achieving an excellent IR protective effect and an excellent UV protective effect, the total content of the component (A) and the component (B) in the external skin preparation (I) is preferably 1.2% by mass or more, more preferably 5% by mass or more, even more preferably 10% by mass or more, further more preferably 15% by mass or more, and the upper limit thereof is 100% by mass. The total content of the component (A) and the component (B) in the external skin preparation (I) is, from the viewpoint of a sense of natural appearance when applied to skin, and a good adhesion of makeup after applied to skin, and from the viewpoint of suppressing a feeling of squeakiness, preferably 80% by mass or less, more preferably 60% by mass or less, even more preferably 50% by mass or less.

The external skin preparation (II) of the present invention can contain the above-mentioned UV absorbent (B) from the viewpoint of improving the UV protective effect thereof.

The component (B) is preferably an organic UV absorbent except the nonvolatile oil (D) and the volatile oil (D)' to be mentioned below, for which an oil-soluble organic UV absorbent or a water-soluble organic UV absorbent can be used. From the viewpoint of achieving an UV protective effect, a sense of natural appearance when applied to skin, and a good adhesion of makeup after applied to skin, and from the viewpoint of preventing stickiness, the component (B) is preferably an oil-soluble organic UV absorbent. Also from the viewpoint of achieving the advantageous effects of the present invention, preferably, the component (B) does not contain an inorganic UV absorbent such as, for example, a UV absorbent prepared by coating the surface of an inorganic filler with a UV absorbent material.

In the case where the external skin preparation (II) contains the component (B), the content thereof is, from the viewpoint of achieving an excellent UV protective effect, preferably 0.5% by mass or more in the external skin preparation (II), more preferably 1% by mass or more, even more preferably 1.5% by mass or more, further more preferably 2% by mass or more, further more preferably 2.5% by mass or more. Also from the viewpoint of satisfying both an excellent IR protective effect and a good adhesion of makeup after applied to skin, the content is preferably 30% by mass or less, more preferably 25% by mass or less, even more preferably 20% by mass or less, further more preferably 15% by mass or less, further more preferably 10% by mass or less, further more preferably 7% by mass or less, further more preferably 5% by mass or less. A specific range of the content of the component (B) in the external skin preparation (II) is, from the viewpoint of satisfying an excellent IR protective effect and an excellent UV protective effect, and also a good adhesion of makeup after applied to skin, preferably 0.5% by mass or more and 30% by mass or less, more preferably 1% by mass or more and 25% by mass or less, even more preferably 1.5% by mass or more and 20% by mass or less, further more preferably 2% by mass or more and 15% by mass or less, further more preferably 2.5% by mass or more and 10% by mass or less, further more preferably 2.5% by mass or more and 7% by mass or less, further more preferably 2.5% by mass or more and 5% by mass or less.

<UV Scattering Agent (C)>

The external skin preparation (II) of the present invention contains a UV scattering agent as a component (C) from the viewpoint of achieving a UV protective effect.

The component (C) is preferably inorganic particles as highly effective in scattering UV rays, and is more preferably metal oxide particles except the component (A). The metal oxide particles include titanium oxide, zinc oxide, iron oxide, zirconium oxide and aluminum oxide except the component (A), and are preferably those of one or more kinds selected from the group consisting of titanium oxide and zinc oxide except the component (A).

The inorganic particles for use for the UV scattering agent are, from the viewpoint of dispersibility in the external skin preparation, preferably those hydrophobized by surface treatment. Examples of surface treatment for hydrophobization include silicone treatment; fluorine treatment with a perfluoroalkyl phosphate, a perfluoroalcohol, etc.; amino acid treatment with an N-acylglutamic acid, etc.; silane compound treatment; silazane treatment; lecithin treatment; metal soap treatment; fatty acid treatment; alkyl phosphate treatment; and inorganic compound treatment, etc. One or more kinds of such surface treatment methods can be used.

The silicone for use in silicone treatment includes methylhydrogen polysiloxane (hydrogen dimethicone), methylpolysiloxane (dimethicone), and methylhydrogen polysiloxane-dimethylpolysiloxane copolymer. Among these, from the viewpoint of enhancing the dispersibility of the component (C) in the external skin preparation, methylpolysiloxane is preferred.

For example, as described in JP 3187440, a method of silicone treatment includes coating a metal oxide such as a zinc oxide powder with a silicone compound (but excepting a silane compound) in a non-gas phase, and then firing it in an oxygen-containing atmosphere at 600 to 950° C. to thereby coat the surface of the metal oxide.

The silane compound for use for silane compound treatment is preferably a silane compound that has an alkyl group or a fluoroalkyl group having 1 or more and 20 or less carbon atoms and is reactive with a metal oxide, and specifically includes a silane compound represented by the following general formula (I):

$$R^AR^B_nSiY_{3-n} \quad (I)$$

wherein n represents an integer of 0 or 1, $R^A$ represents a linear or branched alkyl or fluoroalkyl group having 1 or more and 20 or less carbon atoms, $R^B$ represents an alkyl group having 1 or more and 6 or less carbon atoms, Y represents a halogen atom or an alkoxy group.

The silazane compound for use for silazane treatment is preferably a silazane compound that has an alkyl group or a fluoroalkyl group having 1 or more and 20 or less carbon atoms and is reactive with a metal oxide, and specifically includes a silazane compound represented by the following general formula (II):

$$R^CR^DR^ESiNHSiR^FR^GR^H \quad (II)$$

wherein $R^C$ to $R^H$ each independently represent a linear or branched alkyl or fluoroalkyl group having 1 or more and 20 or less carbon atoms.

Specific examples of the silane compound include hexyltrimethoxysilane, octyltrimethoxysilane, decyltrimethoxysilane, octadecyltrimethoxysilane, octyltriethoxysilane, trifluoropropyltrimethoxysilane, and heptadecafluorodecyltrimethoxysilane. Among these, from the viewpoint of enhancing the dispersibility of the component (C) in the external skin preparation, one or more selected from the group consisting of octyltriethoxysilane and octyltrimethoxysilane are preferred.

Specific examples of the silazane compound include hexamethyldisilazane, and octyldisilazane, and from the viewpoint of enhancing the dispersibility of the component (C) in the external skin preparation, hexamethyldisilazane is preferred.

An example of silane compound treatment or silazane treatment is a method including mixing a silane compound or a silazane compound with metal oxide particles and the like for use as a UV scattering agent, in an organic solvent such as n-hexane, cyclohexane or a lower alcohol, then optionally finely pulverizing the resultant mixture, and removing the organic solvent by heating under reduced pressure followed by further heat treatment preferably at 80 to 250° C. In that manner, a silane compound or a silazane compound is chemically reacted on the surfaces of the metal oxide particles.

In addition, as described in JP 2007-326902 A, also employable is a surface treatment method including coating metal oxide particles and the like for use as a UV scattering agent with a specific polysiloxane compound and then surface-treating them by using alkylalkoxysilane in water.

The fatty acid for use for fatty acid treatment includes a fatty acid having 8 or more and 22 or less carbon atoms, preferably having 12 or more and 18 or less carbon atoms. The fatty acid may be saturated or unsaturated, or linear or branched, but is preferably a linear saturated fatty acid. Specific examples of the fatty acid include caprylic acid, pelargonic acid, capric acid, lauric acid, myristic acid, palmitic acid, stearic acid, oleic acid, linolic acid, linolenic acid, arachic acid, arachidonic acid, and behenic acid. Among these, one or more selected from the group consisting of lauric acid, myristic acid, palmitic acid and stearic acid are preferred, and stearic acid is more preferred.

The inorganic compound for use for inorganic compound treatment includes a silicon compound and an aluminum compound, and specific examples thereof include silica, alumina, and aluminum hydroxide. Among these, from the viewpoint of suppressing the surface activity of metal oxide particles used as the component (C), one or more selected from the group consisting of alumina and aluminum hydroxide are preferred.

Surface treatment for the component (C) is preferably one or more selected from the group consisting of silicone treatment, silane compound treatment, silazane treatment, fatty acid treatment and inorganic compound treatment, more preferably one or more selected from the group consisting of silicone treatment, fatty acid treatment and inorganic compound treatment, even more preferably one or more selected from the group consisting of silicone treatment, and a combination of fatty acid treatment and inorganic acid treatment.

In the case where the component (C) is a surface-treated one, the coating amount with a surface-treating agent is, from the viewpoint of enhancing the dispersibility thereof in the external skin preparation, preferably 3% by mass or more, more preferably 5% by mass or more relative to the total amount of the UV scattering agent, and is, from the viewpoint of enhancing the dispersibility of the component (C) in the external skin preparation, preferably 15% by mass or less, more preferably 10% by mass or less. A specific range of the coating amount is preferably 3% by mass or more and 15% by mass or less, more preferably 5% by mass or more and 10% by mass or less. Falling within the range, the surfaces of metal oxide particles can be uniformly coated with a surface-treating agent to hardly cause aggregation or precipitation of the surface-treating agent used.

The shape of the particles of the component (C) may be spherical, rod-shaped, spindle-shaped, acicular, tabular or amorphous, and is not specifically limited so far as the particles achieve a UV scattering effect.

The number-average particle diameter of the component (C) is generally 1 nm or more, and is, from the viewpoint of achieving an excellent UV protective effect, preferably 5 nm or more, more preferably 8 nm or more, even more preferably 10 nm or more. Also from the viewpoint of a sense of natural appearance when applied to skin, it is preferably 500 nm or less, more preferably 300 nm or less even more preferably 100 nm or less, further more preferably 60 nm or less.

The number-average particle diameter is determined by measuring the largest minor axis of each of 300 particles in an image taken with a transmission electron microscope (TEM) under the condition of 100,000 magnifications and averaging the resultant data to give an average value. Here, the largest minor axis means a minor axis having a largest diameter that crosses a major axis of a particle at right angles.

The component (C) for use herein may be commercial products. Examples of commercial products of titanium oxide particles usable as the component (C) except the component (A) include "MT-100TV®" (aluminum hydroxide, treated with stearic acid) and "MTY-110M3S®" (aluminum hydroxide, treated with silica and hydrogen dimethicone) from TAYCA Corporation.

Examples of commercial products of zinc oxide particles for use as the component (C) include "FINEX-50-LPTM®" (treated with dimethicone), "FINEX-25®" (with no surface treatment) and "FINEX-25LP®" (treated with dimethicone) from Sakai Chemical Industry Co., Ltd., and "MZ-300®" (with no surface treatment), "MZ-504R3M®" (treated with hydrogen dimethicone), "MZY-303S®" (treated with hydrogen dimethicone), "MZ-306X®" (treated with triethoxysilylethyl polydimethylsiloxyethyl hexyl dimethicone), "MZ-200®" (with no surface treatment), "MZY-203S®" (treated with hydrogen dimethicone", "MZ-150®" (with no surface treatment), "MZY-153S®" (treated with hydrogen dimethicone), "MZ-505S®" and "MZY-505S®" from TAYCA Corporation.

One alone or two or more kinds of the components (C) can be used either singly or as combined.

The ratio by mass of the component (A) to the component (C) [(A)/(C)] in the external skin preparation (II) of the present invention is, from the viewpoint of achieving an excellent IR protective effect and an excellent UV protective effect, and from the viewpoint of a sense of natural appearance when applied to skin, and a good adhesion of makeup after applied to skin, 0.1 or more, preferably 0.5 or more, more preferably 0.85 or more, even more preferably 1.2 or more, further more preferably 1.5 or more, further more preferably 1.8 or more. Also from the viewpoint of a sense of natural appearance when applied to skin, and a good adhesion of makeup after applied to skin, the ratio by mass [(A)/(C)] is 18 or less, preferably 15 or less, more preferably 8 or less, even more preferably 5 or less, further more preferably 3 or less, further more preferably 2.5 or less. A specific range of the ratio by mass of the component (A) to the component (C) [(A)/(C)] in the external skin preparation (II) is, from the viewpoint of achieving an excellent IR protective effect and an excellent UV protective effect, and from the viewpoint of satisfying both a sense of natural appearance when applied to skin and a good adhesion of makeup after applied to skin, 0.1 or more and 18 or less, preferably 0.5 or more and 15 or less, more preferably 0.5 or more and 8 or less, even more preferably 0.5 or more and 5 or less, further more preferably 0.85 or more and 3 or less, further more preferably 1.2 or more and 2.5 or less, further more preferably 1.5 or more and 2.5 or less, further more preferably 1.8 or more and 2.5 or less.

The content of the component (C) in the external skin preparation (II) of the present invention is not specifically limited so far as its amount is to make the ratio by mass [(A)/(C)] fall 0.1 or more and 18 or less, but is, from the viewpoint of achieving an excellent IR protective effect and an excellent UV protective effect, preferably 0.5% by mass or more, more preferably 2% by mass or more, even more preferably 3% by mass or more. Also from the viewpoint of a sense of natural appearance when applied to skin, and a good adhesion of makeup after applied to skin, the content is preferably 20% by mass or less, more preferably 12% by mass or less, even more preferably 8% by mass or less. A specific range of the content of the UV scattering agent in the external skin preparation (II) is, from the viewpoint of achieving an excellent IR protective effect and an excellent UV protective effect, and from the viewpoint of satisfying both a sense of natural appearance when applied to skin and a good adhesion of makeup after applied to skin, preferably 0.5% by mass or more and 20% by mass or less, more preferably 2% by mass or more and 12% by mass or less, even more preferably 3% by mass or more and 12% by mass or less, further more preferably 3% by mass or more and 8% by mass or less.

From the viewpoint of further enhancing the UV protective effect thereof, the external skin preparation (I) of the present invention may contain the above-mentioned UV scattering agent (C).

In the case where the external skin preparation (I) of the present invention contain the UV scattering agent (C), the content thereof is, from the viewpoint of the UV protective effect, preferably 1% by mass or more, more preferably 3% by mass or more, even more preferably 5% by mass or more. Also from the viewpoint of achieving easy spreadability on skin and smoothness when applied to skin, the content is preferably 20% by mass or less, more preferably 18% by mass or less, even more preferably 15% by mass or less. A specific range of the UV scattering agent in the external skin preparation (I) is preferably 1% by mass or more and 20% by mass or less, more preferably 3% by mass or more and 18% by mass or less, even more preferably 5% by mass or more and 15% by mass or less.

(Nonvolatile Oil (D))

The external skin preparation (II) of the present invention contains a nonvolatile oil (D) from the viewpoint of dispersibility of the UV scattering agent (C) therein.

In the case where the external skin preparation (I) of the present invention contains an oil-soluble UV absorbent (B), preferably, the preparation (I) further contains a nonvolatile oil (I)) from the viewpoint of solubility of the component (B) therein.

The nonvolatile oil is an oily agent except the UV absorbent (B) and is such that the amount of evaporation thereof, as measured according to the method (1) mentioned below, is less than 20% at 25° C. for 6 hours.

Method (1): A piece of filter paper having a diameter of 90 mm is put in a glass laboratory dish having a diameter of 120 mm, 1 g of a sample is put on the filter paper, and stored in room (25° C.) at 65% RH. After 6 hours, the residue of the sample is measured, and the amount of evaporation thereof is calculated.

Also preferably, the component (D) is liquid under one atmospheric pressure at 25° C. More specifically, the viscosity at 25° C. of the component (D) is preferably 500 mPa·s or less, more preferably, 300 mPa·s or less, even more preferably 100 mPa·s or less, further more preferably 50 mPa·s or less, and is preferably 5 mPa·s or more.

The viscosity is measured using a B-type viscometer "TVB-10" (from Toki Sangyo Co., Ltd.) with a rotor No. 1, at 25° C. and 60 rpm for 1 minute.

Specifically, the component (D) is a nonvolatile oil liquid at 25° C. except the component (B), and examples thereof include an ester oil, a silicone oil, a hydrocarbon oil, a higher fatty acid, and a higher alcohol.

Examples of the nonvolatile liquid ester oil include one or more selected from the group consisting of isononyl isononanoate, isotridecyl isononanoate, isopropyl myristate, isocetyl myristate, octyldodecyl myristate, isopropyl palmitate, ethylhexyl palmitate, 2-hexyldecyl palmitate, glyceryl tri-2-ethylhexanoate, di-2-ethylhexyl sebacate, diisopropyl sebacate, glyceryl tri (caprylate/caprate), diisostearyl malate, diethylene glycol dicaprylate, neopentyl glycol dicaprate, neopentyl glycol di-2-ethylhexanoate, alkyl benzoates such as alkyl (C12 to C15) benzoates, etc.

Among the above, from the viewpoint of a sense of natural appearance when applied to skin, a good adhesion of makeup after applied to skin, and little stickiness, a monoester of a fatty acid having 12 or more and 18 or less carbon atoms and a branched alcohol having 2 or more and 22 or less carbon atoms, a triester of a branched fatty acid having 6 or more and 18 or less carbon atoms and glycerin, a diester of a dicarboxylic acid having 2 or more and 18 or less carbon atoms and a branched alcohol having 2 or more and 18 or less carbon atoms, a diester of a fatty acid having 6 or more and 18 or less carbon atoms and a branched dialcohol having 2 or more and 10 or less carbon atoms, an alkyl (C12 to C15) benzoate (e.g., Finsolv TNG, by Innospec Active Chemicals LLC) and the like are preferred; and specifically, one or more selected from the group consisting of isopropyl myristate, isocetyl myristate, octyldodecyl myristate, isopropyl palmitate, ethylhexyl palmitate, 2-hexyldecyl palmitate, glyceryl tri-2-ethylhexanoate, diisopropyl sebacate, di-2-ethylhexyl sebacate, diisostearyl malate, neopentyl glycol di-2-ethylhexanoate, neopentyl glycol dicaprate, and alkyl (C12 to C15) benzoates are more preferred; and one or more selected from the group consisting of isopropyl palmitate and alkyl (C12 to C15) benzoates are even more preferred.

The nonvolatile liquid silicone oil is, from the viewpoint of suppressing stickiness when applied to skin, preferably a methylpolysiloxane, and more preferably a methylpolysiloxane having a viscosity at 25° C.' of 20 mPa·s or less.

The nonvolatile liquid hydrocarbon oil includes liquid paraffin, light liquid isoparaffin such as hydrogenated polyisobutene, heavy liquid isoparaffin, liquid ozokerite, squalane, pristane, squalene, isohexadecane, etc. Among these, from the viewpoint of suppressing stickiness when applied to skin, one or more selected from the group consisting of light liquid isoparaffin and isohexadecane are preferred, and light fluid isoparaffin is more preferred.

The nonvolatile liquid higher fatty acid includes a fatty acid having 12 or more and 22 or less carbon atoms, specifically oleic acid, isostearic acid, linolic acid, linoleic acid, etc.

The nonvolatile liquid higher alcohol includes an alcohol having 12 or more and 28 or less carbon atoms, specifically oleyl alcohol, 2-decyl-tetradecanol, dodecanol, isostearyl alcohol, octyl dodecanol, etc.

Of the nonvolatile oil that is liquid at 25° C., the component (D) is, from the viewpoint of suppressing stickiness when applied to skin, preferably one or more selected from the group consisting of an ester oil, a silicone oil and a hydrocarbon oil.

In the case of the external skin preparation (I), one or more selected from the group consisting of an ester oil and a hydrocarbon oil are more preferred, and one or more selected from the group consisting of alkyl (C12-15) benzoates, isopropyl palmitate and light liquid isoparaffin are even more preferred.

In the case of the external skin preparation (II), a silicone oil is more preferred, and methylpolysiloxane is even more preferred.

In the case where the external skin preparation (I) of the present invention contains the component (D), the content thereof is, from the viewpoint of achieving an excellent IR protective effect and an excellent UV protective effect, and from the viewpoint of a sense of natural appearance when applied to skin, and a good adhesion of makeup after applied to skin, preferably 1% by mass or more, more preferably 5% by mass or more, even more preferably 15% by mass or more, and is, from the viewpoint of a good adhesion of makeup after applied to skin, preferably 40% by mass or less, more preferably 35% by mass or less, even more preferably 25% by mass or less. A specific range of the content of the component (I)) in the external skin preparation (I) is, from the viewpoint of achieving an excellent IR protective effect and an excellent UV protective effect, and from the viewpoint of satisfying both a sense of natural appearance when applied to skin and a good adhesion of makeup after applied to skin, preferably 1% by mass or more and 40% by mass or less, more preferably 5% by mass or more and 35% by mass or less, even more preferably 15% by mass or more and 25% by mass or less.

In the case where the external skin preparation (I) of the present invention contains the component (D), the ratio by mass [(A)/(D)] is, from the viewpoint of achieving an excellent IR protective effect and an excellent UV protective effect, and from the viewpoint of a sense of natural appearance when applied to skin and a good adhesion of makeup after applied to skin, preferably 0.1 or more, more preferably 0.2 or more, even more preferably 0.35 or more, further more preferably 0.4 or more, and is, from the viewpoint of a sense of natural appearance when applied to skin and a good adhesion of makeup after applied to skin, preferably 5 or less, more preferably 3 or less, even more preferably 2 or less, further more preferably 1.3 or less, further more preferably 0.75 or less, further more preferably 0.6 or less. A specific range of the ratio by mass [(A)/(D)] in the external skin preparation (1) is, from the viewpoint of achieving an excellent IR protective effect and an excellent UV protective effect, and from the viewpoint of satisfying both a sense of natural appearance when applied to skin and a good adhesion of makeup after applied to skin, preferably 0.1 or more and 5 or less, more preferably 0.1 or more and 3 or less, even more preferably 0.2 or more and 2 or less, further more preferably 0.2 or more and 1.3 or less, further more preferably 0.35 or more and 0.75 or less, further more preferably 0.4 or more and 0.6 or less.

In the case where the external skin preparation (I) of the present invention contains the component (D), the ratio by mass [(B)/(D)] is, from the viewpoint of achieving an excellent IR protective effect and an excellent UV protective effect, and from the viewpoint of a good adhesion of makeup after applied to skin, preferably 0.1 or more, more preferably 0.2 or more, even more preferably 0.3 or more, further more preferably 0.45 or more, and is, from the viewpoint of a sense of natural appearance when applied to skin, and a good adhesion of makeup after applied to skin, preferably 4 or less, more preferably 2 or less, even more preferably 1.5 or less, further more preferably 0.75 or less. A specific range of the ratio by mass [(B)/(I))] in the external skin preparation (I) is, from the viewpoint of achieving an excellent IR protective effect and an excellent UV protective effect, and from the viewpoint of satisfying both a sense of natural appearance when applied to skin and a good adhesion of makeup after applied to skin, preferably 0.1 or more and 4 or less, more preferably 0.2 or more and 2 or less, even more preferably 0.3 or more and 1.5 or less, further more preferably 0.45 or more and 1.5 or less, further more preferably 0.45 or more and 0.75 or less.

The content of the component (D) in the external skin preparation (II) of the present invention is, from the viewpoint of achieving an excellent IR protective effect and an excellent UV protective effect, and from the viewpoint of a sense of natural appearance when applied to skin, and a good adhesion of makeup after applied to skin, preferably 1% by mass or more, more preferably 5% by mass or more, even more preferably 15% by mass or more, further more preferably 20% by mass or more, further more preferably 25% by mass or more, and is, from the same viewpoints, preferably 45% by mass or less, more preferably 38% by mas or less, even more preferably 35% by mass or less. A specific range of the content of the component (D) in the external skin preparation (II) is, from the same viewpoints, preferably 1% by mass or more and 45% by mass or less, more preferably 5% by mass or more and 38% by mass or less, even more preferably 5% by mass or more and 38% by mas or less, further more preferably 15% by mass or more and 38% by mass or less, further more preferably 20% by mass or more and 35% by mass or less, further more preferably 25% by mass or more and 35% by mass or less.

In the external skin preparation (II) of the present invention, the ratio by mass [A)/(D)] is, from the viewpoint of achieving an excellent IR protective effect and an excellent UV protective effect, and from the viewpoint of satisfying both a sense of natural appearance when applied to skin and a good adhesion of makeup after applied to skin, preferably 0.1 or more, more preferably 0.2 or more, even more preferably 0.28 or more, and the ratio by mass [(A)/(D)] is, from the same viewpoint, preferably 2 or less, more preferably 0.75 or less, even more preferably 0.5 or less, further more preferably 0.45 or less. A specific range of the ratio by mass [(A)/(D)] in the external skin preparation (II) is, also from the same viewpoint, preferably 0.1 or more and 2 or less, more preferably 0.1 or more and 0.75 or less, even more preferably 0.1 or more and 0.5 or less, further more preferably 0.2 or more and 0.45 or less, further more preferably 0.28 or more and 0.45 or less.

In the external skin preparation (II) of the present invention, the ratio by mass [(C)/(D)] is, from the viewpoint of achieving an excellent IR protective effect and an excellent UV protective effect, and from the viewpoint of satisfying both a sense of natural appearance when applied to skin and a good adhesion of makeup after applied to skin, preferably 0.02 or more, more preferably 0.025 or more, even more preferably 0.1 or more, and is, from the same viewpoint, preferably 5 or less, more preferably 3 or less, even more preferably 1 or less, further more preferably 0.8 or less, further more preferably 0.1 or less. A specific range of the ratio by mass [(C)/(D)] in the external skin preparation (II) is, from the same viewpoint, preferably 0.02 or more and 5 or less, more preferably 0.025 or more and 3 or less, even more preferably 0.025 or more and 1 or less, further more preferably 0.025 or more and 0.8 or less, further more preferably 0.1 or more and 0.8 or less, further more preferably 0.1 or more and 0.4 or less.

In the external skin preparation (II) of the present invention, the ratio by mass of the total content of the component (A) and the component (C) to the content of the component (I)) [(A+C)/(D))] is, from the viewpoint of achieving an excellent IR protective effect and an excellent UV protective effect, and from the viewpoint of satisfying both a sense of natural appearance when applied to skin and a good adhesion of makeup after applied to skin, preferably 0.30 or more, more preferably 0.35 or more, even more preferably 0.40 or more, further more preferably 0.45 or more. Also from the same viewpoint, the ratio is preferably 2.0 or less, more preferably 1.5 or less, even more preferably 1.0 or less, further more preferably 0.75 or less, further more preferably 0.70 or less. A specific range of the ratio by mass of the total content of the component (A) and the component (C) to the content of the component (D) [(A+C)/(D)] in the external skin preparation (II) is, from the same viewpoint, preferably 0.30 or more and 2.0 or less, more preferably 0.30 or more and 1.5 or less, even more preferably 0.30 or more and 1.0 or less, further more preferably 0.35 or more and 0.75 or less, further more preferably 0.40 or more and 0.70 or less, further more preferably 0.45 or more and 0.70 or less.

(Volatile Oil (D)')

The external skin preparations (1) and (II) of the present invention may further contains a volatile oil as a component (I))'. The volatile oil is an oily agent except the above-mentioned UV absorbent (B), and is such that the amount of evaporation thereof, as measured according to the method (1) mentioned below, is 20% or more at 25° C. for 6 hours.

Method (1): A piece of filter paper having a diameter of 90 mm is put in a glass laboratory dish having a diameter of 120 mm, 1 g of a sample is put on the filter paper, and stored in room (25° C.) at 65% RH. After 6 hours, the residue of the sample is measured, and the amount of evaporation thereof is calculated.

The component (D)' is preferably a volatile silicone oil, more preferably a linear organopolysiloxane and a cyclic organopolysiloxane that are liquid and volatile at 25° C.

Specific examples of the linear organopolysiloxane include octamethyltrisiloxane, decamethyltetrasiloxane, dodeacmethylpentasiloxane, and 1,1,1,3,5,5,5-heptamethyl-3-[(trimethylsilyl)oxy]-trisiloxane.

The cyclic organopolysiloxane includes a 4- to 6-membered cyclic siloxane having an alkyl group with 1 or more and 5 or less carbon atoms as a substituent, and specific examples thereof include octamethylcyclotetrasiloxane and decamethylcyclopentasiloxane.

Among the above, the component (D)' is, from the viewpoint of little stickiness when applied to skin, preferably a cyclic organopolysiloxane, more preferably decamethylcyclopentasiloxane.

The volatile silicone oils usable as the component (D)' include octamethyltrisiloxane ("KF-96A-1cs®)"), decamethyltetrasiloxane ("KF-96L-1.5cs®)"), dodecamethylpentasiloxane ("KF-96L-2cs®"), decamethylcyclopentasiloxane ("KF-995"), and 1,1,1,3,5,5,5-heptamethyl-3-[(trimethylsilyl)oxy]-trisiloxane ("TMF-1.5"), each commercial product available from Shin-Etsu Chemical Co., Ltd.: octamethyltrisiloxane ("SH200C Fluid 1cs®"), decamethyltetrasiloxane ("SH200C Fluid 1.5cs®"), dodecamethylpentasiloxane ("SH200C Fluid 2cs®"), and decamethylcyclopentasiloxane ("SH245 Fluid®"), each commercial product available from DuPont Toray Specialty Materials K.K.; and decamethylcyclopentasiloxane ("TSF405"), commercial product available from Momentive Performance Materials Corporation.

In the case where the external skin preparation (1) of the present invention contains the component (D)', the content thereof is, from the viewpoint of achieving an excellent IR protective effect and an excellent UV protective effect, and from the viewpoint of a sense of natural appearance when applied to skin, a good adhesion of makeup after applied to skin, and a stickiness preventive effect, preferably 10% by mass or more, more preferably 20% by mass or more, even more preferably 25% by mass or more, and is preferably 75% by mass or less, more preferably 70% by mass or less, even more preferably 60% by mass or less. A specific range of the content of the component (D)' in the external skin preparation (I) is preferably 10% by mass or more and 75% by mass or less, more preferably 20% by mass or more and 70% by mass or less, even more preferably 25% by mass or more and 60% by mass or less.

In the case where the external skin preparation (II) of the present invention contains the component (D)', the content thereof is, from the viewpoint of achieving an excellent IR protective effect and an excellent UV protective effect, and from the viewpoint of a sense of natural appearance when applied to skin, a good adhesion of makeup after applied to skin, and a stickiness preventive effect, preferably 5% by mass or more, more preferably 10% by mass or more, even more preferably 20% by mass or more, and is preferably 75% by mass or less, more preferably 70% by mass or less, even more preferably 60% by mass or less. A specific range of the content of the component (D)' in the external skin preparation (II) is preferably 5% by mass or more and 75% by mass or less, more preferably 10% by mass or more and 70% by mass or less, even more preferably 20% by mass or more and 60% by mass or less.

(Surfactant (E))

Preferably, the external skin preparations (I) and (II) of the present invention further contain a surfactant (E), from the viewpoint of satisfying both an IR protective effect and a UV protective effect, and a sense of natural appearance when applied to skin, and from the viewpoint of dispersing oily components in water or dispersing water-soluble components in oil.

As the component (E), a known surfactant is employable, and examples thereof include an anionic surfactant, a cationic surfactant, an ampholytic surfactant and a nonionic surfactant. In addition, a fluorine-based surfactant and a silicone-based surfactant are also employable.

Preferably, the external skin preparations of the present invention contain at least a silicone-based surfactant from the viewpoint of satisfying both an IR protective effect and a sense of natural appearance when applied to skin, and from the viewpoint of dispersing oily components in water or dispersing water-soluble components in oil, more preferably a nonionic silicone-based surfactant.

Examples of the silicone-based surfactant include polyether-modified silicones represented by the following general formulae (1) to (3):

(1)

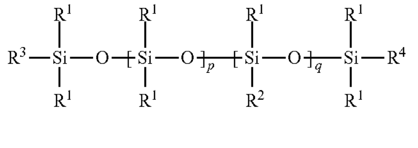

wherein $R^1$ represents an alkyl group having 1 or more and 5 or less carbon atoms, or a phenyl group; $R^2$ represents a group represented by a formula $—(CH_2)_r—O—(C_2H_4O)_a—(C_3H_6O)_t—R^5$ (where $R^5$ represents a hydrogen atom or an alkyl group having 1 or more and 5 or less carbon atoms, r represents a number of 1 or more and 5 or less, s represents a number of 1 or more and 50 or less, t represents a number of 0 or more and 30 or less); $R^3$ and $R^4$ each represent the same group as any one of $R^1$ or $R^2$; p represents a number of 5 or more and 300 or less; q represents a number of 1 or more and 50 or less; provided that all $R^1$'s are not to be a phenyl group.

(2)

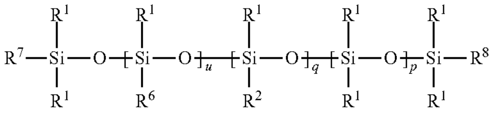

wherein $R^1$, $R^2$, p and q are the same as above; $R^6$ represents an alkyl group having 2 or more and 20 or less carbon atoms; $R^7$ and $R^8$ each represent the same group as any one of $R^1$, $R^2$ or $R^6$; u represents a number of 1 or more and 30 or less; provided that all $R^1$'s are not to be a phenyl group.

(3)

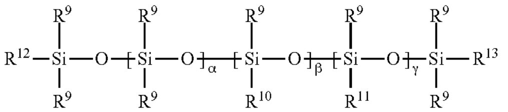

wherein $R^9$ represents an alkyl group having 1 or more and 4 or less carbon atoms; $R^{10}$ represents a group represented by a formula $-Q^1-O-(C_2H_4O)_x-(C_3H_6O)_yR^{14}$ (where $Q^1$ represents a divalent hydrocarbon group having 1 or more and 4 or less carbon atoms; $R^{14}$ represents a hydrogen atom, an alkyl group having 1 or more and 4 or less carbon atoms, or an acetyl group; x represents a number of 1 or more; y represents a number of 0 or more); $R^{11}$ represents a group represented by a formula $-Q^2-O-R^{15}$ (where $Q^2$ represents a divalent hydrocarbon group having 1 or more and 4 or less carbon atoms; $R^{15}$ represents a hydrocarbon group having 8 or more and 30 or less carbon atoms); $R^{12}$ and $R^{13}$ each represent the same group as any one of $R^9$, $R^{10}$ or $R^{11}$; α represents a number of 0 or more; β and γ each represent a number of 1 or more.

In the polyether-modified silicone represented by the general formulae (1) to (3), the silicone chain can have a branched structure, or the silicone can be co-modified with any other functional group than polyether, within a range not overstepping the intended purpose.

Examples of commercial products of the polyether-modified silicone represented by the general formula (1) include "KF-6015®" and "KF-6017®" from Shin-Etsu Chemical Co., Ltd.: "SH3775M®" (polyoxyethylene/methylpolysiloxane copolymer) and "SH3772C®" from DuPont Toray Specialty Materials K.K. The polyether-modified silicone represented by the general formula (2) includes a so-called alkylpolyether-modified silicone, and examples of commercial products thereof include "Abil® WE-09" from Goldschmidt AG; and "KF-6038®" from Shin-Etsu Chemical Co., Ltd. The polyether-modified silicone represented by the general formula (3) includes a polyoxyalkylene alkyl ether-co-modified organopolysiloxane, which can be readily produced by co-modifying a methylhydrogen polysiloxane with a poly oxyalkylene allyl ether and an allyl alkyl ether.

A partially-crosslinked polyether-modified silicone can also be used as a silicone-based surfactant. Such a partially-crosslinked polyether-modified silicone is one prepared by addition polymerization of an organohydrogen polysiloxane and an aliphatic unsaturated group-containing compound, and examples thereof are described in JP 4-272932 A and JP 5-140320 A.

The partially crosslinked polyether-modified organopolysiloxane polymer is a polymer composed of, as essential components, a component of the following general formula (4) and/or a component of the following general formula (a), in a combination of an organohydrogen polysiloxane represented by the following general formula (4):

$$R^{16}_aR^{17}_bH_cSiO_{(4-a-b-c)/2} \quad (4)$$

wherein $R^{16}$ represents an alkyl group, an aryl group, an aralkyl group or a halogenohydrocarbon group optionally having a substituent having 1 or more and 18 or less carbon atoms; $R^{17}$ represents a polyoxyalkylene group represented by a formula $-C_nH_{2n}O(C_2H_4O)_d(C_3H_6O)_eR^{18}$ (where $R^{18}$ represents a hydrogen atom, a saturated aliphatic hydrocarbon group having 1 or more and 10 or less carbon atoms, or a monovalent group represented by $-C(O)-R^{19}$ (where $R^{19}$ represents a saturated aliphatic hydrocarbon group having 1 or more and 5 or less carbon atoms), d represents a number of 2 or more and 200 or less, e represents a number of 0 or more and 200 or less, d+e is a number of 3 or more and 200 or less, n represents a number of 2 or more and 6 or less), a is $1 \leq a \leq 2.5$, b is $0.001 \leq b \leq 1$, c is $0.001 \leq c \leq 1$; and/or an organohydrogen polysiloxane represented by the following general formula (5):

$$R^{16}_fH_gSio_{(1-f-g)/2} \quad (5)$$

wherein $R^{16}$ is the same as above, f is $1 \leq f \leq 3$, g is $0.001 \leq g \leq 1.5$; and a polyoxyalkylene represented by the following general formula (a):

$$C_mH_{2m+1}O(C_2H_4O)_h(C_3H_6O)_iC_mH_{2m-1} \quad (a)$$

wherein h represents a number of 2 or more and 200 or less, i represents a number of 0 or more and 200 or less, h+i is a number of 3 or more and 200 or less, m represents a number of 2 or more and 6 or less; and/or an organopolysiloxane represented by the following general formula (b):

$$R^{16}_jR^{20}_kSiO_{(4-j-k)/2} \quad (b)$$

wherein $R^{16}$ is the same as above, $R^{20}$ represents a monovalent hydrocarbon having 2 or more and 10 or less carbon atoms and having an aliphatic unsaturated group at the terminal, j is $1 \leq j \leq 3$, k is $0.001 \leq k \leq 1.5$.

The other surfactant than the silicone-based surfactant is preferably a nonionic surfactant, more preferably a polyoxyethylene alkyl ether-based nonionic surfactant. Examples of the nonionic surfactant include polyoxyethylene (21) lauryl ether ("Emulgen® 121-G"), polyoxyethylene (20)2-hexyldecyl ether ("Emulgen® 1620G"), and polyoxyethylene(20) octyldodecyl ether ("Emulgen® 2020G"), each commercial product available from Kao Corporation.

As the component (E), one or more kinds can be used either singly or as combined. Among the above, the component (E) is preferably one or more silicone-based surfactants selected from the group consisting of polyether-modified silicones represented by the general formulae (1) to (3), more preferably a silicone-modified surfactant of a polyether-modified silicone represented by the general formula (1).

In the case where the external skin preparations (I) and (II) of the present invention contain the component (E), the content thereof is, from the viewpoint of satisfying both an IR protective effect and a UV protective effect, and a sense of natural appearance when applied to skin, and from the viewpoint of dispersing oily components in water or dispersing water-soluble components in oil, preferably 0.1% by mass or more, more preferably 0.3% by mass or more, even more preferably 0.5% by mass or more, and is preferably 15% by mass or less, more preferably 10% by mass or less, even more preferably 5% by mass or less, further more preferably 1.5% by mass or less. A specific range of the content of the component (E) in the external skin preparations (I) and (II) of the present invention is preferably 0.1% by mass or more and 15% by mass or less, more preferably 0.3% by mass or more and 10% by mass or less, even more preferably 0.3% by mass or more and 5% by mass or less, further more preferably 0.5% by mass or more and 1.5% by mass or less.

(Aqueous Medium)

The external skin preparations (I) and (II) of the present invention may further contain an aqueous medium from the viewpoint of dispersing the component (A) and dispersing or dissolving other formulation ingredients to improve applicability to skin. The aqueous medium is not specifically limited so far as it can disperse or dissolve the component (A) and other formulation ingredients, and examples thereof include water; a monoalcohol having 4 or less carbon atoms such as ethanol, isopropyl alcohol and butyl alcohol; and a low-molecular diol or triol having 6 or less carbon atoms such as 1,3-butylene glycol, glycerin, ethylene glycol, propylene glycol, diethylene glycol, and dipropylene glycol. Among these, one or more selected from the group consisting of water and a monoalcohol having 4 or less carbon atoms are preferred, and one or more selected from the group consisting of water and ethanol are more preferred.

The content of the aqueous medium in the external skin preparation can be appropriately selected depending on the form of the external skin preparation.

In the case of the external skin preparation (I), the content of the aqueous medium is preferably 5% by mass or more, more preferably 8% by mass or more, even more preferably 10% by mass or more, and is preferably 98.8% by mass or less, more preferably 90% by mass or less, even more preferably 70% by mass or less, further more preferably 50% by mass or less. A specific range of the content of the aqueous medium in the external skin preparation (I) is preferably 5% by mass or more and 98.8% by mass or less, more preferably 8% by mass or more and 90% by mass or less, even more preferably 10% by mass or more and 70% by mass or less, further more preferably 10% by mass or more and 50% by mass or less.

In the case of the external skin preparation (II), the content of the aqueous medium is preferably 1% by mass or more, more preferably 3% by mass or more, even more preferably 5% by mass or more, and is preferably 97.5% by mass or less, more preferably 90% by mass or less, even more preferably 70% by mass or less, further more preferably 50% by mass or less. A specific range of the content of the aqueous medium in the external skin preparation (II) is preferably 1% by mass or more and 97.5% by mass or less, more preferably 3% by mass or more and 90% by mass or less, even more preferably 5% by mass or more and 70% by mass or less, further more preferably 5% by mass or more and 50% by mass or less.

<Other Components>

The external skin preparation of the present invention can contain, as needed, any other component than the above-mentioned components, for example, an antiperspirant, a fragrance, a moisturizer, a tackifier, a germicide, a pH regulator, an antioxidant, and a preservative.

(Production Method for External Skin Preparation)

A production method for the external skin preparation of the present invention is not specifically limited, and depending on the form of the external skin preparation, any known method can be appropriately employed. For example, in the case of the external skin preparation (I), all the components (A) and (B) and the other components can be blended, and in the case of the external skin preparation (II), all the components (A), (C) and (D) and the other components can be blended, and uniformly mixed using a disperser or the like. Alternatively, all the other component than the aqueous medium are blended, then uniformly mixed with a disperser or the like, and thereafter the aqueous medium can be mixed and stirred using a homogenizer or the like.

[IR and UV Protecting Method for Skin]

The present invention also provides an IR or UV protecting method for skin, including applying the external skin preparation (I) or (II) of the present invention to skin. The protecting method of the present invention is not specifically limited so far as the method includes a step of applying the external skin preparation (I) or (II) of the present invention to skin.

In the protecting method of the present invention, the IR protection factor at a wavelength of 1500 nm is preferably 10% or more, more preferably 12% or more, even more preferably 15% or more. When the IR protection factor at a wavelength of 1500 nm is 10% or more, the external skin preparation can realize an actual sensation of high-level heat insulation. The IR protection factor (%) is a value represented by 100-X (%) in which X (%) means an IR transmissivity measured with a spectrophotometer, and specifically, it is measured according to the method described in the section of Examples.

By applying the external skin preparation of the present invention to skin, the skin can be effectively protected from both IR and UV rays. Regarding the UV protective effect, the external skin preparation (I) preferably has an SPF value of 10 or more, more preferably 20 or more, even more preferably 30 or more.

The external skin preparation (II) preferably has an SPF value of 3 or more, more preferably 5 or more, even more preferably 7.5 or more, further more preferably 10 or more.

Specifically, the SPF value can be measured according to the method described in the section of Examples.

Regarding the above-mentioned embodiments, the present invention further discloses the following embodiments.

<1>

An external skin preparation containing a tabular metal oxide (A) having a thickness of 30 nm or more and 360 nm or less and an aspect ratio of 50 or more and 300 or less, and a UV absorbent (B) in a ratio [(A)/(B)] by mass of 0.1 or more and 5 or less, preferably 0.3 or more and 3.5 or less, more preferably 0.3 or more and 2.3 or less, even more preferably 0.55 or more and 1.5 or less, further more preferably 0.55 or more and 1.2 or less, further more preferably 0.7 or more and 1.2 or less.

<2>

An external skin preparation containing a tabular metal oxide (A) having a thickness of 30 nm or more and 360 nm or less and an aspect ratio of 50 or more and 300 or less, a UV scattering agent (C) and a nonvolatile oil (D) in a ratio [(A)/(C)] by mass of 0.1 or more and 18 or less, preferably 0.5 or more and 15 or less, more preferably 0.5 or more and 8 or less, even more preferably 0.5 or more and 5 or less further more preferably 0.85 or more and 3 or less, further more preferably 1.2 or more and 2.5 or less, further more preferably 1.5 or more and 2.5 or less, further more preferably 1.8 or more and 2.5 or less.

<3>

The external skin preparation according to <1> or <2>, wherein the thickness of the component (A) is preferably 50 nm or more, more preferably 60 nm or more, even more preferably 80 nm or more, further more preferably 105 nm or more, further more preferably 125 nm or more, and is preferably 330 nm or less, more preferably 310 nm or less, even more preferably 280 nm or less, further more preferably 270 nm or less, further more preferably 230 nm or less, further more preferably 150 nm or less.

<1>

The external skin preparation according to any one of <1> to <3>, wherein the aspect ratio of the component (A) is preferably 55 or more, more preferably 65 or more, even more preferably 70 or more, further more preferably 100 or more, and is preferably 230 or less, more preferably 200 or less, even more preferably 140 or less, further more preferably 125 or less, further more preferably 120 or less.

<5>

The external skin preparation according to any one of <1> to <4>, wherein the metal oxide to constitute the component (A) is preferably one or more selected from the group consisting of titanium oxide, zinc oxide, zirconium oxide, iron oxide, aluminum oxide and cerium oxide, more preferably one or more selected from the group consisting of titanium oxide and zinc oxide, even more preferably titanium oxide.

<6>

The external skin preparation according to any one of <1> to <5>, wherein the content of the component (A) is preferably 1% by mass or more, more preferably 3% by mass or more, even more preferably 6% by mass or more, further more preferably 8% by mass or more, and is preferably 35% by mass or less, more preferably 25% by mass or less, even more preferably 17% by mass or less, further more preferably 12% by mass or less.

<7>

The external skin preparation according to any one of <1> to <6>, wherein the component (B) is an oil-soluble organic UV absorbent, preferably one or more selected from the group consisting of 2-ethylhexyl p-methoxycinnamate, 4-tert-butyl-4'-methoxydibenzoylmethane, octocrylene, 2-ethylhexyl dimethoxybenzylidene dioxoimidazolidine propionate, hexyl diethylaminohydroxybenzoyl benzoate, bis-ethylhexyloxyphenol methoxyphenyl triazine, methylene bis-benzotriazolyl tetramethylbutylphenol, and 2,4,6-tris[4-(2-ethylhexyloxycarbonyl)anilino]-1,3,5-triazine, more preferably one or more selected from the group consisting of 2-ethylhexyl p-methoxycinnamate, hexyl diethylaminohydroxybenzoyl benzoate, bis-ethylhexyloxyphenol methoxyphenyl triazine, and 2,4,6-tris[4-(2-ethylhexyloxycarbonyl)anilino]-1,3,5-triazine, even more preferably one or more selected from the group consisting of 2-ethylhexyl p-methoxycinnamate, hexyl diethylaminohydroxybenzoyl benzoate, and bis-ethylhexyloxyphenol methoxyphenyl triazine, further more preferably a combination of two or more of these.

<8>

The external skin preparation according to any one of <1> to <7>, wherein the content of the component (B) is preferably 0.2% by mass or more, more preferably 1.5% by mass or more, even more preferably 5% by mass or more, further more preferably 7% by mass or more, and is preferably 30% by mass or less, more preferably 25% by mass or less, even more preferably 20% by mass or less, further more preferably 15% by mass or less.

<9>

The external skin preparation according to any one of <1> to <8>, wherein the total content of the component (A) and the component (B) is preferably 1.2% by mass or more, more preferably 5% by mass or more, even more preferably 10% by mass or more, further more preferably 15% by mass or more, and is 100% by mass or less.

<10>

The external skin preparation according to any one of <2> to <9>, wherein the component (C) is preferably metal oxide particles except the component (A), and the metal oxide is more preferably one or more selected from the group consisting of titanium oxide, zinc oxide, iron oxide, zirconium oxide and aluminum oxide except the component (A), more preferably one or more selected from the group consisting of titanium oxide and zinc oxide except the component (A).

<11>

The external skin preparation according to any one of <2> to <10>, wherein the number-average particle size of the component (C) is 1 nm or more, preferably 5 nm or more, more preferably 8 nm or more, even more preferably 10 nm or more, and is preferably 500 nm or less, more preferably 300 nm or less, even more preferably 100 nm or less, further more preferably 60 nm or less.

<12>

The external skin preparation according to any one of <2> to <11>, wherein the content of the component (C) is preferably 0.5% by mass or more, more preferably 2% by mass or more, even more preferably 3% by mass or more, and is preferably 20% by mass or less, more preferably 12% by mass or less, even more preferably 8% by mass or less.

<13>

The external skin preparation according to any one of <1>, and <3> to <12>, further containing a nonvolatile oil (D), whose content is preferably 1% by mass or more, more preferably 5% by mass or ore, even more preferably 15% by mass or ore, and is preferably 40% by mass or less, more preferably 35% by mass or less, even more preferably 25% by mass or less.

<14>

The external skin preparation according to <13>, wherein the component (I)) is one or more selected from the group consisting of an ester oil, a silicone oil, a hydrocarbon oil, a higher fatty acid, and a higher alcohol, preferably one or more selected from the group consisting of an ester oil, a silicone oil and a hydrocarbon oil, more preferably one or more selected from the group consisting of an ester oil and a hydrocarbon oil, even more preferably one or more selected from the group consisting of an alkyl (C12-15) benzoate, isopropyl palmitate, and light liquid isoparaffin.

<15>

The external skin preparation according to <13> or <14>, wherein the ratio by mass [(A)/(D)] is preferably 0.1 or more, more preferably 0.2 or more, even more preferably 0.3 or more, further more preferably 0.45 or more, and is preferably 4 or less, more preferably 2 or less, even more preferably 1.5 or less, further more preferably 0.75 or less.

<16>

The external skin preparation according to any one of <13> to <15>, wherein the ratio by mass [(B)/(D)] is preferably 0.1 or more, more preferably 0.2 or more, even more preferably 0.3 or more, further more preferably 0.45 or more, and is preferably 4 or less, more preferably 2 or less, even more preferably 1.5 or less, further more preferably 0.75 or less.

<17>

The external skin preparation according to any one of <2> to <12>, wherein the component (D) is one or more selected from the group consisting of an ester oil, a silicone oil, a hydrocarbon oil, a higher fatty acid, and a higher alcohol, preferably one or more selected from the group consisting of an ester oil, a silicone oil and a hydrocarbon oil, more preferably a silicone oil, even more preferably a methylpolysiloxane.

<18>

The external skin preparation according to any one of <2> to <12> and <17>, wherein the content of the component (D) is preferably 1% by mass or more, more preferably 5% by mass or more, even more preferably 15% by mass or more, further more preferably 20% by mass or more, further more preferably 25% by mass or more, and is preferably 45% by mass or less, more preferably 38% by mass or less, even more preferably 35% by mass or less.

<19>

The external skin preparation according to any one of <2> to <12>, <17> and <18>, wherein the ratio by mass [(A)/(D)] is preferably 0.1 or more, more preferably 0.2 or more, even more preferably 0.28 or more, and is preferably 2 or less, more preferably 0.75 or less, even more preferably 0.5 or less, further more preferably 0.45 or less.

<20>

The external skin preparation according to any one of <2> to <12>, and <17> to <19>, wherein the ratio by mass [(B)/(D)] is preferably 0.02 or more, more preferably 0.025 or more, even more preferably 0.1 or more, and is preferably 5 or less, more preferably 3 or less, even more preferably 1 or less, further more preferably 0.8 or less, further more preferably 0.4 or less.

<21>

The external skin preparation according to any one of <2> to <12>, and <17> to <20>, wherein the ratio by mass [(A+C)/(D)] is preferably 0.30 or more, more preferably 0.35 or more, even more preferably 0.40 or more, further more preferably 0.45 or more, and is preferably 2.0 or less, more preferably 1.5 or less, even more preferably 1.0 or less, further more preferably 0.75 or less, further more preferably 0.70 or less.

<22>

The external skin preparation according to any one of <2> to <12>, and <17> to <21>, further containing a UV absorbent (B), whose content is preferably 0.5% by mass or more, more preferably 1% by mass or more, even more preferably 1.5% by mass or more, further more preferably 2% by mass or more, further more preferably 2.5% by mass or more and is preferably 30% by mass or less, more preferably 25% by mass or less, even more preferably 20% by mass or less, further more preferably 15% by mass or less, further more preferably 10% by mass or less, further more preferably 7% by mass or less, further more preferably 5% by mass or less.

<23>

The external skin preparation according to <22>, wherein the component (B) is an oil-soluble organic UV absorbent, preferably one or more selected from the group consisting of 2-ethylhexyl p-methoxycinnamate, 4-tert-butyl-4'-methoxydibenzoylmethane, octocrylene, 2-ethylhexyl dimethoxybenzylidene dioxoimidazolidine propionate, hexyl diethylaminohydroxybenzoyl benzoate, bis-ethylhexyloxyphenol methoxyphenyl triazine, methylene bis-benzotriazolyl tetramethylbutylphenol, and 2,4,6-tris[4-(2-ethylhexyloxycarbonyl)anilino]-1,3,5-triazine, more preferably one or more selected from the group consisting of 2-ethylhexyl p-methoxycinnamate, hexyl diethylaminohydroxybenzoyl benzoate, bis-ethylhexyloxyphenol methoxyphenyl triazine, and 2,4,6-tris[4-(2-ethylhexyloxycarbonyl)anilino]-1,3,5-triazine, even more preferably, one or more selected from the group consisting of 2-ethylhexyl p-methoxycinnamate, hexyl diethylaminohydroxybenzoyl benzoate, and bis-ethylhexyloxyphenol methoxyphenyl triazine, further more preferably a combination of two or more of these.

<24>

The external skin preparation according to any one of <1> to <23>, further containing a volatile oil (D)', whose content is preferably 5% by mass or more, more preferably 10% by mass or more, even more preferably 20% by mass or more, further more preferably 25% by mass or more, and is preferably 75% by mass or less, more preferably 70% by mass or less, even more preferably 60% by mass or less.

<25>

The external skin preparation according to <24>, wherein the component (D)' is a volatile silicone oil, preferably one or more selected from a linear organopolysiloxane and a cyclic organopolysiloxane, more preferably a cyclic organopolysiloxane, even more preferably a decamethylcyclopentasiloxane.

<26>

The external skin preparation according to any one of <1> to <25>, further containing a surfactant (E) whose content is preferably 0.1% by mass or more, more preferably 0.3% by mass or more, even more preferably 0.5% by mass or more, and is preferably 15% by mass or less, more preferably 10% by mass or less, even more preferably 5% by mass or less, further more preferably 1.5% by mass or less.

<27>

The external skin preparation according to <26>, wherein the component (E) contains at least a silicone-based surfactant, and preferably contains a nonionic silicone-based surfactant.

<28>

An external skin preparation containing one or more kinds of a tabular meal oxide (A) selected from the group consisting of a tabular titanium oxide and a tabular zinc oxide having a thickness of 80 nm or more and 280 nm or less, and a UV absorbent (B), wherein the content of the component (A) is 6% by mass or more and 35% by mass or less, and the ratio by mass [(A)/(B)] is 0.1 or more and 5 or less.

<29>

An external skin preparation containing one or more kinds of a tabular meal oxide (A) selected from the group consisting of a tabular titanium oxide and a tabular zinc oxide having a thickness of 80 nm or more and 280 nm or less, and a UV absorbent (B) and a nonvolatile oil (D), wherein the content of the component (A) is 6% by mass or more and 17% by mass or less, and the ratio by mass [(A)/(B)] is 0.55 or more and 1.5 or less.

<30>

An external skin preparation containing one or more kinds of a tabular meal oxide (A) selected from the group consisting of a tabular titanium oxide and a tabular zinc oxide having a thickness of 80 nm or more and 280 nm or less, and a UV scattering agent (C) and a nonvolatile oil (D)), wherein the ratio by mass [(A)/(C)] is 0.85 or more and 3 or less, the ratio by mass [(A)/(D)] is 0.2 or more and 0.45 or less, and the ratio by mass [(A+C)/(D)] is 0.35 or more and 0.75 or less.

<31>

The external skin preparation according to any one of <1> to <30>, which is a skin cosmetic material.

<32>

An IR and UV protecting method for skin, including applying the external skin preparation of any one of <1> to <31> to skin.

EXAMPLES

Hereinunder the present invention is described with reference to Examples, but the present invention is not limited to the range of Examples. In Examples, measurement and evaluation were carried out according to the following methods.

(Measurement of Thickness, Major Diameter and Aspect Ratio)

The thickness, the major diameter and the aspect ratio of the component (A) and the inorganic particles except the component (A) (expressed as "component (A)" in Tables) were measured by observation with a scanning electron microscope ("VE-9800" from Keyence Corporation) under the condition of an acceleration voltage of 10 keV and an observation power of 10,000 magnifications.

The thickness of the component (A) and the tabular component (A)' was determined by measuring the thickness of 50 particles in an observation image and calculating the average value thereof per number. The aspect ratio was determined by measuring the thickness and the major diameter of 50 particles, then calculating the aspect ratio (major diameter/thickness) of each particle, and averaging the data to give an average value of aspect ratio.

(Number-Average Particle Diameter of Component (C))

The number-average particle diameter of the component (C) was determined by measuring the largest minor axis (a minor axis having a largest diameter of minor axes crossing a major axis at right angles) of each of 300 particles in an image taken with a transmission electron microscope (TEM) under the condition of 100,000 magnifications and calculating an average value of the data.

(IR Protection Factor)

28.5 mg of the external skin preparation of each Example was applied onto a polymethyl methacrylate resin (PMMA) substrate ("HD6" from Helioscreen Corporation) of 5 cm×5 cm, and dried for 15 minutes to give a test sample. Similarly, glycerin was applied to a PMMA substrate and dried for 15 minutes to give a control sample. Using a spectrophotometer ("UV-3600" from Shimadzu Corporation) in an integrating sphere mode, the transmissivity at a wavelength of 1500 nm of the test sample and the control sample was measured. A value calculated by dividing the transmissivity of the test sample by the transmissivity of the control sample is referred to as a transmissivity X (%), and 100-X (%) is referred to as an IR protection factor. Alarger value means a higher IR protective effect.

(UV Protective Effect (In-Vitro SPF Value))

28.5 mg of the external skin preparation of each Example was applied onto a PMMA substrate ("HD) 6" from Helioscreen Corporation) of 5 cm×5 cm, and dried for 15 minutes to give a test sample. Similarly, glycerin was applied to a PMMA substrate and dried for 15 minutes to give a control sample. Using an SPF analyzer ("UV-2000S" from Labsphere Corporation), an in-vitro SPF value of the test sample was measured after previous measurement by subtracting the transmissivity of the control sample as a blank.

(Sense of Natural Appearance when Applied to Skin)

About 0.1 g of the external skin preparation of each Example was applied to the inner side of the forearm in an area of 2 cm×5 cm, and immediately the skin was observed. When the skin was extremely white and gave an unnatural feel, point 1 was given, and when the skin was naturally white with no unnatural feel, point 5 was given, and the tested sample was evaluated on a five-point scale. Five expert panelists tested every sample, and the given points were averaged to be an evaluation result.

<Evaluation Standards>

1: Extremely white, and gave extremely unnatural feel.

2: Somewhat white, and gave an unnatural feel.

3: Neutral.

4: Naturally white, but gave a little unnatural feel.

5: Naturally white, and did not gave an unnatural feel.

(Good adhesion of makeup after applied to skin)

About 0.1 g of the external skin preparation of each Example was applied to the inner side of the forearm in an area of 2 cm×5 cm, and a powder foundation was applied thereon and evaluated as to "adhesiveness" was given or not. When the applied foundation was non-uniform and was extremely unsmooth, point 1 was given, and when the applied foundation was uniform and was extremely smooth, point 5 was given, and the tested sample was evaluated on a five-point scale. Five expert panelists tested every sample, and the given points were averaged to be an evaluation result.

<Evaluation Standards>

1: Foundation was non-uniform and had bad adhesiveness.

2: Foundation was somewhat non-uniform and had somewhat bad adhesiveness.

3: Neutral.

4: Foundation was somewhat uniform and had somewhat good adhesiveness.

5: Foundation was uniform and had extremely good adhesiveness.

(Comprehensive Evaluation)

In the evaluation results in Table 1, samples having an IR protection factor of 10% or more, an in-vitro SPF value of 10 or more, a sense of natural appearance when applied to skin of 3 or more, and a good adhesion of makeup after applied to skin of 3 or more were accepted as good (Evaluation A), while samples not meeting at least any one evaluation item were evaluated as bad (Evaluation C), and the evaluation results are shown in Table 1.

Production Example 1 (Production of Tabular Titanium Oxide 3a)

A toluene solution of 30% by mass tetra-n-butyl orthotitanate (hereinafter referred to as a first liquid) was introduced into a double tube reactor (inner tube opening size 170 μm, outer tube opening size 400 μm) through the inner tube opening at a flow rate of 0.29 ml/min, and a 1-butyl-3-methylimidazolium bis(trifluoromethylsulfonyl)amide solution (hereinafter referred to as a second liquid) with 1% by mass water dissolved therein through the outer tube opening at a flow rate of 20.8 ml/min, and the two liquids were brought into contact with each other for sol-gel reaction to give a gel of tabular titanium oxide. The temperature (reaction temperature) of the first and second liquids was 25° C., and the contact time (reaction time) at the contact area for the first and second liquids was 3 seconds. The resultant slurry was filtered through a metal mesh, and the tabular titanium oxide gel having remained on the metal mesh was washed with ethanol, then dried and fired to give a solid tabular titanium oxide 3a. Measured according to the above-mentioned method, the thickness of the tabular titanium oxide 3a was 264 nm and the aspect ratio thereof was 57.

Production Example 2 (Production of Comparative Tabular Titanium Oxide 1b)

A comparative tabular titanium oxide 1b was produced in the same manner as in Production Example 1 except that in Production Example 1, the flow rate of the first liquid was 0.14 ml/min, and the flow rate of the second liquid was 10.4 ml/min. Measured according to the above-mentioned method, the thickness of the comparative tabular titanium oxide 1b was 388 nm and the aspect ratio thereof was 39.

Examples I-1 to I-12, Comparative Examples I-1 to I-4 (Production and Evaluation of External Skin Preparations)

Among the components shown in Table 1, all except water and ethanol were blended and mixed uniformly using a disperser. Next, water and ethanol were added to the resultant mixture and uniformly mixed using a homogenizer to give an external skin preparation having a composition shown in Table 1. The resultant external skin preparation was evaluated according to the above-mentioned methods. The results are shown in Table 1. The blending amount shown in Table 1 is the amount (% by mass) of the active ingredient of each component.

TABLE 1

| | | | | Example | | | | | | | | | | | | Comparative Example | | | |
|---|---|---|---|---|---|---|---|---|---|---|---|---|---|---|---|---|---|---|---|
| | | | | I-1 | I-2 | 1-3 | I-4 | I-5 | I-6 | I-7 | 1-8 | I-9 | I-10 | I-11 | I-12 | I-1 | I-2 | I-3 | I-4 |
| Formulation of External Preparation (mass %) | (A) | Tabular Titanium Oxide 1 (thickness 66 nm/ aspect ratio 227) | *1 | 10 | — | — | — | — | — | — | — | — | — | — | — | — | — | — | — |
| | | Tabular Titanium Oxide 2 (thickness 134 nm/ aspect ratio 112) | *2 | — | 10 | — | 5 | 7 | 20 | 30 | 10 | 10 | 10 | 10 | 10 | — | 0.5 | — | 10 |
| | | Tabular Titanium Oxide 3 (thickness 264 nm/ aspect ratio 57) | *3 | — | — | 10 | — | — | — | — | — | — | — | — | — | — | — | — | — |
| | (A)' | Comparative Tabular Titanium Oxide 1 (thickness 388 nm/ aspect ratio 39) | *4 | — | — | — | — | — | — | — | — | — | — | — | — | 10 | — | — | — |
| | | Titanium Oxide-Coated Pearl Pigment (tabular, thickness 110 nm/ aspect ratio 13) | *5 | — | — | — | — | — | — | — | — | — | — | — | — | — | — | 10 | — |
| | (B) | 2-Ethylhexyl p-methoxy-cinnamate | *6 | 8 | 8 | 8 | 8 | 8 | 8 | 8 | 3 | 20 | 8 | 8 | 8 | 8 | 8 | 8 | — |
| | | Hexyl 2-(4-diethyl-amino-2-hydroxy-benzoyl)benzoate | *7 | 2 | 2 | 2 | 2 | 2 | 2 | 2 | 0 | 2 | 2 | 2 | 2 | 2 | 2 | 2 | — |
| | | 2,4-Bis{[4-(2-ethylhexyloxy)-2-hydroxylphenyl}-6-(4-methoxyphenyl)-1,3,5-triazine | *8 | 1 | 1 | 1 | 1 | 1 | 1 | 1 | 0 | 1 | 1 | 1 | 1 | 1 | 1 | 1 | — |
| | (D) | Alkyl benzoate (C12-15) | *9 | 10 | 10 | 10 | 10 | 10 | 10 | 10 | — | — | — | 9 | 20 | 10 | 10 | 10 | 10 |
| | | Isopropyl palmitate | *10 | 5 | 5 | 5 | 5 | 5 | 5 | 5 | — | — | — | — | 5 | 5 | 5 | 5 | 5 |
| | | Light liquid isoparaffin | *11 | 4 | 4 | 1 | 4 | 4 | 4 | 4 | — | — | — | — | 4 | 4 | 4 | 4 | 4 |
| | (D)' | Decamethyl-cyclopentasiloxane | *12 | 27.5 | 27.5 | 27.5 | 27.5 | 27.5 | 27.5 | 27.5 | 46.5 | 46.5 | 46.5 | 37.5 | 27.5 | 27.5 | 27.5 | 27.5 | 38.5 |
| | (E) | Polyoxyethylene/ methylpolysiloxane copolymer | *13 | 0.8 | 0.8 | 0.8 | 0.8 | 0.8 | 0.8 | 0.8 | 0.8 | 0.8 | 0.8 | 0.8 | 0.8 | 0.8 | 0.8 | 0.8 | 0.8 |
| | others | Ethanol | | 11.5 | 11.5 | 11.5 | 11.5 | 11.5 | 11.5 | 11.5 | 11.5 | 11.5 | 11.5 | 11.5 | 11.5 | 11.5 | 11.5 | 11.5 | 11.5 |
| | | Water | | balance | balance | balance | balance | balance | balance | balance | balance | balance | balance | balance | balance | balance | balance | balance | balance |

TABLE 1-continued

| | | Example | | | | | | | | | | | | Comparative Example | | | |
|---|---|---|---|---|---|---|---|---|---|---|---|---|---|---|---|---|---|
| | | I-1 | I-2 | 1-3 | I-4 | I-5 | I-6 | I-7 | 1-8 | I-9 | I-10 | I-11 | I-12 | I-1 | I-2 | I-3 | I-4 |
| | Ratio by mass A/B | 0.91 | 0.91 | 0.91 | 0.45 | 0.64 | 1.82 | 2.73 | 3.33 | 0.43 | 0.91 | 0.91 | 0.91 | — | 0.05 | — | — |
| | Ratio by mass A/D | 0.53 | 0.53 | 0.53 | 0.26 | 0.37 | 1.05 | 1.58 | — | — | — | 1.11 | 0.34 | — | 0.03 | — | 0.53 |
| | Ratio by mass B/D | 0.58 | 0.58 | 0.58 | 0.58 | 0.58 | 0.58 | 0.58 | — | — | — | 1.22 | 0.38 | 0.58 | 0.58 | 0.58 | — |
| Evaluation Results | IR Protection factor (%) | 10.9 | 17.7 | 17.8 | 10.2 | 15.5 | 26.4 | 39.5 | 14.5 | 12.5 | 16.2 | 16.6 | 18.0 | 6.9 | 0.3 | 8.9 | 17.5 |
| | UV Protective Effect (in-vitro SPF value) | 30.5 | 33.0 | 31.4 | 29.3 | 30.7 | 131.7 | 122.4 | 12.3 | 40.1 | 28.6 | 32.7 | 52.6 | 28.2 | 10.3 | 25.0 | 2.9 |
| | Sense of natural appearance | 4 | 5 | 5 | 5 | 5 | 4 | 3 | 4 | 4 | 4 | 5 | 5 | 2.4 | 2 | 3 | 5 |
| | Adhesiveness of makeup after applied to skin | 5 | 5 | 5 | 4 | 5 | 4 | 4 | 4 | 4 | 4 | 5 | 4 | 3 | 2 | 5 | 3 |
| | Comprehensive Evaluation | A | A | A | A | A | A | A | A | A | A | A | A | C | C | C | C |

The blending components in Table 1 are as follows.
*1: "Featheleve PT-9001K" by CQV Co., Ltd., coated with 7.5% by mass of (alkyl acrylate/dimethicone) copolymer.
*2: "Featheleve PT-7801K" by CQV Co., Ltd., coated with 7.5% by mass of (alkyl acrylate/dimethicone) copolymer.
*3: Tabular titanium oxide 3a produced in Production Example 1, coated with 7.5% by mass of (alkyl acrylate/dimethicone) copolymer.
*4: Comparative tabular titanium oxide 1b produced in Production Example 2, coated with 7.5% by mass of (alkyl acrylate/dimethicone) copolymer.
*5: "Flamenco Satin Blue" by BASF SE (thickness of titanium oxide coating layer: 10 nm), coated with 7.5% by mass of (alkyl acrylate/dimethicone) copolymer.
*6: "Uvinul MC80" by BASF SE.
*7: "Uvinul A Plus" by BASF SE.
*8: "Tinosorb S" by BASF SE.
*9: "Finsolv TN" by Innospec Active Chemicals LLC.
*10: "Exeparl IPP" by Kao Corporation.
*11: "Parleam 4" by NOF Corporation, light liquid isoparaffin (hydrogenated polyisobutene).
*12: "TSF405" by Momentive Performance Materials Corporation.
*13: "SH3775M" by DuPont Toray Specialty Materials K.K., polyoxyethylene-methylpolysiloxane copolymer (PEG-12 dimethicone).

As in Table 1, the external skin preparations of Examples I-1 to I-12 can satisfy IR and UV protective effects, and satisfy a good sense of natural appearance when applied to skin, and a good adhesion of makeup after applied to skin. In addition, as not sticky, these are also excellent in a sense of use. Comparing Examples I-1 to I-3 and Comparative Example I-1, it is known that, when a tabular titanium oxide having a predetermined thickness as defined in the present invention is used, there can be provided external skin preparations having a better IR protective effect, and a better sense of natural appearance when applied to skin, and a better adhesion of makeup after applied to skin. In particular, when the component (A) having a thickness falling within a range of 105 nm or more and 270 nm or less, especially within a range of 125 nm or more and 230 nm or less is used, the IR protective effect improves more and additionally the UV protective effect also increases.

As opposed to these, the external skin preparation of Comparative Example I-1 using a tabular titanium oxide whose thickness is more than 360 nm in place of the component (A) has a poor IR protective effect, and when applied to skin and after applied to skin, the sense of natural appearance and the good adhesion of makeup thereof are also poor. Comparative Example I-2 in which the ratio by mass of the component (A) to the component (B) in the external skin preparation [(A)/(B)] is less than 0.1, and Comparative Examples I-3 using tabular inorganic particles except metal oxide in place of the component (A) do not achieve an excellent IR protective effect. The UV protective effect of the external skin preparation of Comparative Example I-4 not containing the component (B) is low.

Examples II-1 to II-16, Comparative Examples II-1 to II-6 (Production and Evaluation of External Skin Preparations)

Among the components shown in Table 2, all except water and ethanol were blended and mixed uniformly using a disperser. Next, water and ethanol were added to the resultant mixture and uniformly mixed using a homogenizer to give an external skin preparation having a composition shown in Table 2. The resultant external skin preparation was evaluated according to the above-mentioned methods. The results are shown in Table 2. The blending amount shown in Table 2 is the amount (% by mass) of the active ingredient of each component.

In the comprehensive evaluation results in Table 2, samples having an IR protection factor of 10% or more, an in-vitro SPF value of 3 or more, a sense of natural appearance when applied to skin of 3.5 or more, and a good adhesion of makeup after applied to skin of 3.5 or more were accepted as good (Evaluation A), while samples not meeting at least any one evaluation item were evaluated as bad (Evaluation C), and the evaluation results are shown in Table 2.

TABLE 2

| | | | | Example | | | | | | | | | | | | | |
|---|---|---|---|---|---|---|---|---|---|---|---|---|---|---|---|---|---|
| | | | | II-1 | II-2 | II-3 | II-4 | II-5 | II-6 | II-7 | II-8 | II-9 | II-10 | II-11 | II-12 | II-13 | II-14 |
| Formulation of External Preparation (mass %) | (A) | Tabular Titanium Oxide 1 (thickness 66 nm/ aspect ratio 227) | *1 | 10 | — | — | — | — | — | — | — | — | — | — | — | — | — |
| | | Tabular Titanium Oxide 2 (thickness 134 nm/ aspect ratio 112) | *2 | — | 10 | — | 10 | 10 | 10 | 5 | 7 | 20 | 30 | 10 | 10 | 10 | 10 |
| | | Tabular Titanium Oxide 3 (thickness 264 nm/ aspect ratio 57) | *3 | — | — | 10 | — | — | — | — | — | — | — | — | — | — | — |
| | (A)' | Comparative Tabular Titanium Oxide 1 (thickness 388 nm/ aspect ratio 39) | *4 | — | — | — | — | — | — | — | — | — | — | — | — | — | — |
| | | Titanium Oxide-Coated Pearl Pigment (tabular, thickness 110 nm/ aspect ratio 13) | *5 | — | — | — | — | — | — | — | — | — | — | — | — | — | — |
| | (C) | Silicone-coated zinc oxide fine particles | *6 | 5 | 5 | 5 | 1 | 10 | 15 | 5 | 5 | 5 | 5 | — | 2.5 | 5 | 5 |
| | | Aluminum hydroxide/ stearic acid-coated titanium oxide fine particles | *7 | — | — | — | — | — | — | — | — | — | — | 5 | 2.5 | — | — |
| | (D) | Methylpolysiloxane | *8 | 30 | 30 | 30 | 30 | 30 | 30 | 30 | 30 | 30 | 30 | 30 | 30 | 10 | 40 |
| | (D)' | Decamethylcyclo-pentasiloxane | *9 | 27.5 | 27.5 | 27.5 | 27.5 | 27.5 | 27.5 | 27.5 | 27.5 | 27.5 | 27.5 | 27.5 | 27.5 | 47.5 | 17.5 |
| | (B) | 2-Ethylhexyl p-methoxycinnamate | *10 | — | — | — | — | — | — | — | — | — | — | — | — | — | — |
| | | Hexyl 2-(4-diethylamino-2-hydroxy-benzoyl)benzoate | *11 | — | — | — | — | — | — | — | — | — | — | — | — | — | — |
| | | 2,4-Bis{[4-(2-ethylhexyloxy)-2-hydroxylphenyl}-6-(4-methoxyphenyl)-1,3,5-triazine | *12 | — | — | — | — | — | — | — | — | — | — | — | — | — | — |

TABLE 2-continued

| | | | | | | | | | | | | | | | | | |
|---|---|---|---|---|---|---|---|---|---|---|---|---|---|---|---|---|---|
| | (E) | Polyoxyethylene-methylpolysiloxane copolymer | *13 | 0.8 | 0.8 | 0.8 | 0.8 | 0.8 | 0.8 | 0.8 | 0.8 | 0.8 | 0.8 | 0.8 | 0.8 | 0.8 | 0.8 |
| | others | Ethanol | | 11.5 | 11.5 | 11.5 | 11.5 | 11.5 | 11.5 | 11.5 | 11.5 | 11.5 | 6.7 | 11.5 | 11.5 | 11.5 | 11.5 |
| | | Water | | balance | balance | balance | balance | balance | balance | balance | balance | balance | balance | balance | balance | balance | balance |
| | Ratio by mass A/C | | | 2.0 | 2.0 | 2.0 | 10.0 | 1.0 | 0.67 | 1.0 | 1.4 | 4.0 | 6.0 | 2.0 | 2.0 | 2.0 | 2.0 |
| | Ratio by mass A/D | | | 0.33 | 0.33 | 0.33 | 0.33 | 0.33 | 0.33 | 0.17 | 0.23 | 0.67 | 1.0 | 0.33 | 0.33 | 1.0 | 0.25 |
| | Ratio by mass C/D | | | 0.17 | 0.17 | 0.17 | 0.033 | 0.33 | 0.50 | 0.17 | 0.17 | 0.17 | 0.17 | 0.17 | 0.17 | 0.50 | 0.13 |
| | Ratio by mass (A + C)/D | | | 0.50 | 0.50 | 0.50 | 0.37 | 0.67 | 0.83 | 0.33 | 0.40 | 0.83 | 1.2 | 0.50 | 0.50 | 1.5 | 0.38 |
| Evaluation Results | IR Protection Factor (%) | | | 17.5 | 21.1 | 22.7 | 18.9 | 19.5 | 20.6 | 12.6 | 17.5 | 35.0 | 36.4 | 20.0 | 18.5 | 20.7 | 17.2 |
| | UV Protective Effect (in vitro SPF value) | | | 7.5 | 8.1 | 8.1 | 3.8 | 15.2 | 22.8 | 7.5 | 8.2 | 29.3 | 25.3 | 10.4 | 8.0 | 8.7 | 6.7 |
| | Sense of natural appearance | | | 4 | 5 | 5 | 5 | 5 | 4 | 5 | 5 | 4 | 3.6 | 5 | 5 | 4 | 4 |
| | Adhesiveness of makeup after applied to skin | | | 5 | 5 | 5 | 5 | 5 | 4 | 4 | 5 | 4 | 3.6 | 5 | 5 | 4 | 4 |
| | Comprehensive Evaluation | | | A | A | A | A | A | A | A | A | A | A | A | A | A | A |

| | | | | Example | | Comparative Example | | | | | |
|---|---|---|---|---|---|---|---|---|---|---|---|
| | | | | II-15 | II-16 | II-1 | II-2 | II-3 | II-4 | II-5 | II-6 |
| Formulation of External Preparation (mass %) | (A) | Tabular Titanium Oxide 1 (thickness 66 nm/ aspect ratio 227) | *1 | — | — | — | — | — | — | — | — |
| | | Tabular Titanium Oxide 2 (thickness 134 nm/ aspect ratio 112) | *2 | 10 | 10 | — | — | 10 | 10 | 10 | 0.1 |
| | | Tabular Titanium Oxide 3 (thickness 264 nm/ aspect ratio 57) | *3 | — | — | — | — | — | — | — | — |
| | (A)' | Comparative Tabular Titanium Oxide 1 (thickness 388 nm/ aspect ratio 39) | *4 | — | — | 10 | — | — | — | — | — |
| | | Titanium Oxide-Coated Pearl Pigment (tabular, thickness 110 nm/ aspect ratio 13) | *5 | — | — | — | 10 | — | — | — | — |
| | (C) | Silicone-coated zinc oxide fine particles | *6 | 5 | 5 | 5 | 5 | — | 5 | 0.5 | 5 |
| | | Aluminum hydroxide/ stearic acid-coated titanium oxide fine particles | *7 | — | — | — | — | — | — | — | — |

TABLE 2-continued

| | | | | | | | | | | | |
|---|---|---|---|---|---|---|---|---|---|---|---|
| | (D) | Methylpolysiloxane | *8 | 30 | 30 | 30 | 30 | 30 | — | 30 | 3 |
| | (D)' | Decamethylcyclo-pentasiloxane | *9 | 24.5 | 7.5 | 27.5 | 27.5 | 27.5 | 57.5 | 57.5 | 57.5 |
| | (B) | 2-Ethylhexyl p-methoxycinnamate | *10 | 3 | 20 | — | — | — | — | — | — |
| | | Hexyl 2-(4-diethylamino-2-hydroxy-benzoyl)benzoate | *11 | — | 2 | — | — | — | — | — | — |
| | | 2,4-Bis{[4-(2-ethylhexyloxy)-2-hydroxylphenyl}-6-(4-methoxyphenyl)-1,3,5-triazine | *12 | — | 1 | — | — | — | — | — | — |
| | (E) | Polyoxyethylene-methylpolysiloxane copolymer | *13 | 0.8 | 0.8 | 0.8 | 0.8 | 0.8 | 0.8 | 0.8 | 0.8 |
| | others | Ethanol | | 11.5 | 11.5 | 11.5 | 11.5 | 11.5 | 11.5 | 11.5 | 11.5 |
| | | Water | | balance | balance | balance | balance | balance | balance | balance | balance |
| | Ratio by mass A/C | | | 2.0 | 2.0 | 0.0 | 0.0 | — | 2.0 | 20.0 | 0.020 |
| | Ratio by mass A/D | | | 0.33 | 0.33 | 0.0 | 0.0 | 0.33 | — | 0.33 | 0.033 |
| | Ratio by mass C/D | | | 0.17 | 0.17 | 0.17 | 0.17 | 0.0 | — | 0.017 | 1.7 |
| | Ratio by mass (A + C)/D | | | 0.50 | 0.50 | 0.50 | 0.50 | 0.33 | — | 0.35 | 1.7 |
| Evaluation Results | | IR Protection Factor (%) | | 16.2 | 15.1 | 7.2 | 9.4 | 18.2 | 16.3 | 17.5 | 2.3 |
| | | UV Protective Effect (in vitro SPF value) | | 22.2 | 150.5 | 9.1 | 7.6 | 2.1 | 6.5 | 2.5 | 6.8 |
| | | Sense of natural appearance | | 5 | 5 | 3 | 3 | 5 | 3 | 5 | 3 |
| | | Adhesiveness of makeup after applied to skin | | 5 | 4 | 3 | 5 | 5 | 3 | 5 | 2 |
| | | Comprehensive Evaluation | | A | A | C | C | C | C | C | C |

The blending components in Table 2 are as follows.
*1: "Featheleve PT-9001K" by CQV Co., Ltd., coated with 7.5% by mass of (alkyl acrylate/dimethicone) copolymer.
*2: "Featheleve PT-7801K" by CQV Co., Ltd., coated with 7.5% by mass of (alkyl acrylate/dimethicone) copolymer.
*3: Tabular titanium oxide 3a produced in Production Example 1, coated with 7.5% by mass of (alkyl acrylate/dimethicone) copolymer.
*4: Comparative tabular titanium oxide 1b produced in Production Example 2, coated with 7.5% by mass of (alkyl acrylate/dimethicone) copolymer.
*5: "Flamenco Satin Blue" by BASF SE (thickness of titanium oxide coating layer: 10 nm), coated with 7.5% by mass of (alkyl acrylate/dimethicone) copolymer.
*6: "MZ-505S" by TAYCA Corporation, number-average particle diameter: 25 nm.
*7: "MT-100TV" by TAYCA Corporation, number-average particle diameter: 15 nm.
*8: "Silicone KF-96A-10cs" by Shin-Etsu Chemical Co., Ltd.
*9: "TSF405" by Momentive Performance Materials Corporation.
*10: "Uvinul MC80" by BASF SE.
*11: "Uvinul A Plus" by BASF SE.
*12: "Tinosorb S" by BASF SE.
*13: "SH3775M" by DuPont Toray Specialty Materials K.K., polyoxyethylene-methylpolysiloxane copolymer (PEG-12 dimethicone).

As in Table 2, the external skin preparations of Examples II-1 to II-16 can satisfy IR and UV protective effects, and satisfy a good sense of natural appearance when applied to skin, and a good adhesion of makeup after applied to skin. For example, comparing Examples II-1 to II-3 and Comparative Example II-1, it is known that, when a tabular titanium oxide having a predetermined thickness as defined in the present invention is used, there can be provided external skin preparations having a better IR protective effect, and a better sense of natural appearance when applied to skin, and a better adhesion of makeup after applied to skin. In particular, when the component (A) having a thickness falling within a range of 80 nm or more and 280 nm or less is used, the IR protective effect improves more and additionally the UV protective effect also increases synergistically.

As opposed to these, the external skin preparation of Comparative Example II-1 using a tabular titanium oxide whose thickness is more than 360 nm in place of the component (A) has a poor IR protective effect, and when applied to skin and after applied to skin, the sense of natural appearance and the good adhesion of makeup thereof are also poor. Comparative Example II-2 using tabular inorganic particles except metal oxide in place of the component (A) does not achieve an excellent IR protective effect.

Comparative Example II-3 not containing the component (C) and Comparative Example II-4 not containing the component (D) have a poor UV protective effect. When applied to skin and after applied to skin, the sense of natural appearance and the good adhesion of makeup of the external skin preparation of Comparative Example II-4 are poor.

Comparative Example II-5 in which the ratio by mass of the component (A) to the component (C) [(A)/(C)] in the external skin preparation is more than 18, and Comparative Example II-6 in which the ratio by mass [(A)/(C)] is less than 0.1 both do not achieve an excellent UV protective effect and an excellent IR protective effect.

INDUSTRIAL APPLICABILITY

The external skin preparation of the present invention is excellent in an IR and UV protective effect, and when applied to skin, hardly whitens and can give a natural appearance, and after applied, secures a good adhesion of makeup, and is excellent in a sense of use with little stickiness, and is therefore useful, for example, as a skin cosmetic material.

The invention claimed is:

1. An external skin preparation, comprising:

a tabular titanium oxide (A) having a thickness of from 125 nm to 360 nm and an aspect ratio of from 50 to 300;

one or more UV absorbent (B) selected from the group consisting of 2-ethylhexyl p-methoxycinnamate, 4-tert-butyl-4'-methoxy dibenzoylmethane, octocrylene, 2-ethylhexyl dimethoxybenzylidene dioxoimidazolidine propionate, hexyl diethylaminohydroxybenzoyl benzoate, bis-ethylhexyloxyphenol methoxyphenyl triazine, methylene bis-benzotriazolyl tetramethylbutylphenol, and 2,4,6-tris[4-(2-ethylhexyloxycarbonyl)anilino]-1,3,5-triazine; and one or more nonvolatile oil (D) selected from the group consisting of isononyl isononanoate, isotridecyl isononanoate, isopropyl myristate isocetyl myristate, octyldodecyl myristate, isopropyl palmitate ethylhexyl palmitate, 2-hexyldecyl palmitate glyceryl tri-2-ethylhexanoate, di-2-ethylhexyl sebacate, diisopropyl sebacate, glyceryl tri (caprylate/caprate), diisostearyl malate, diethylene glycol dicaprylate, neopentyl glycol dicaprate, neopentyl glycol di-2-ethylhexanoate, an alkyl (C12 to C15) benzoate, a silicone oil, and a hydrocarbon oil, wherein a content of the tabular titanium oxide (A) is from 3% by mass to 35% by mass, wherein a mass ratio (A)/(B) is from 0.1 to 3.5, wherein a mass ratio (A)/(D) is from 0.1 to 2, wherein an IR protection factor is 10% or more, and wherein the IR protection factor is defined by 100%-X (%), where X (%) is a value calculated by dividing the transmissivity at 1500 nm wavelength of the external skin preparation by the transmissivity at 1500 nm wavelength of an equivalent mass of glycerin.

2. The external skin preparation according to claim 1, further comprising:

a tabular zinc oxide.

3. The external skin preparation according to claim 1, which is a skin cosmetic material.

4. A method for protecting a skin from IR rays and UV rays, the method comprising applying the external skin preparation of claim 1 to the skin.

5. The external skin preparation according to claim 1, further comprising:

one or more UV scattering agent (C) selected from the group consisting of surface treated titanium oxide particles and surface treated zinc oxide particles, wherein the surface treated titanium oxide particles and the surface treated zinc oxide particles are treated with a compound selected from the group consisting of dimethicone, hydrogen dimethicone, triethoxysilylethyl polydimethylsiloxyethyl hexyl dimethicone, stearic acid, and aluminum hydroxide.

6. An external skin preparation, comprising:

a tabular titanium oxide (A) having a thickness of from 125 nm to 360 nm and an aspect ratio of from 50 to 300; and one or more UV absorbent (B) selected from the group consisting of 2-ethylhexyl pmethoxycinnamate, hexyl diethylaminohydroxybenzoyl benzoate, and bisethylhexyloxyphenol methoxyphenyl triazine; and one or more nonvolatile oil (D) selected from the group consisting of an alkyl (C12-15) benzoate, isopropyl palmitate, and hydrogenated polyisobutene, wherein a mass ratio (A)/(B) is from 0.1 to 3.5, wherein a mass ratio (A)/(D) is from 0.1 to 2, wherein an IR protection factor is 10% or more, and wherein the IR protection factor is defined by 100%-X (%), where X (%) is a value calculated by dividing the transmissivity at 1500 nm wavelength of the external skin preparation by the transmissivity at 1500 nm wavelength of an equivalent mass of glycerin.

7. The external skin preparation according to claim 6, wherein a content of the tabular titanium oxide (A) is from 1% by mass to 35% by mass.

8. The external skin preparation according to claim 6, further comprising:

a tabular zinc oxide.

9. The external skin preparation according to claim 6, which is a skin cosmetic material.

10. A method for protecting a skin from IR rays and UV rays, the method comprising applying the external skin preparation of claim 6 to the skin.

11. The external skin preparation according to claim 6, further comprising:

one or more UV scattering agent (C) selected from the group consisting of surface treated titanium oxide particles and surface treated zinc oxide particles, wherein the surface treated titanium oxide particles and the surface treated zinc oxide particles are treated with a compound selected from the group consisting of dimethicone, hydrogen dimethicone, triethoxysilylethyl polydimethylsiloxyethyl hexyl dimethicone, stearic acid, and aluminum hydroxide.

* * * * *